(12) United States Patent
Collin

(10) Patent No.: US 7,351,418 B2
(45) Date of Patent: *Apr. 1, 2008

(54) COSMETIC COMPOSITION COMPRISING A POLYMER BLEND

(75) Inventor: Nathalie Collin, Sceaux (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/993,430

(22) Filed: Nov. 22, 2004

(65) Prior Publication Data

US 2005/0089505 A1 Apr. 28, 2005

Related U.S. Application Data

(63) Continuation of application No. 10/012,029, filed on Dec. 11, 2001, now Pat. No. 6,835,399.

(60) Provisional application No. 60/280,844, filed on Apr. 3, 2001.

(30) Foreign Application Priority Data

Dec. 12, 2000 (FR) .................................... 00 16161

(51) Int. Cl.
*A61Q 19/00* (2006.01)
*A61Q 1/04* (2006.01)
*A61Q 1/10* (2006.01)
*A61Q 1/08* (2006.01)
*A61Q 5/00* (2006.01)

(52) U.S. Cl. .......................... 424/401; 424/59; 424/61; 424/63; 424/64; 424/69; 424/70.1; 424/70.7; 424/70.11

(58) Field of Classification Search ..................... None
See application file for complete search history.

(56) References Cited

U.S. PATENT DOCUMENTS

| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway |
| 3,141,787 A | 7/1964 | Goetze et al. |
| 3,148,125 A * | 9/1964 | Havass et al. ................. 424/64 |
| 3,156,572 A | 11/1964 | Carlick et al. |
| 3,157,681 A | 11/1964 | Fischer |
| 3,255,082 A | 6/1966 | Barton |
| 3,324,041 A | 6/1967 | Sommer et al. |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,247,411 A | 1/1981 | Vanlerberghe et al. |
| 4,275,054 A | 6/1981 | Sebag et al. |
| 4,275,055 A | 6/1981 | Nachtigal et al. |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,367,390 A | 1/1983 | Balleys et al. |
| 4,376,194 A | 3/1983 | Tanaka et al. |
| 4,387,090 A | 6/1983 | Bolich, Jr. |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |

(Continued)

FOREIGN PATENT DOCUMENTS

CA 2003346 5/1990

(Continued)

OTHER PUBLICATIONS

English language Derwent abstract for JP 49-75740.

(Continued)

*Primary Examiner*—Jyothsna Venkat
(74) *Attorney, Agent, or Firm*—Finnegan, Henderson, Farabow, Garrett & Dunner L.L.P.

(57) ABSTRACT

Cosmetic composition comprising a polymer blend The invention relates to a composition comprising, in a physiologically acceptable medium, at least a first polymer with a weight-average molecular mass of less than 100 000, comprising a) a polymer skeleton containing hydrocarbon-based repeating Units containing at least one hetero atom, and optionally b) at least one pendent fatty chain and/or at least one terminal fatty chain, which may be functionalized, containing from 6 to 120 carbon atoms and being linked to these hydrocarbon-based units, a dispersion of particles of a second film-forming polymer that is insoluble in said medium. Application to make-up and caring for keratin materials.

44 Claims, No Drawings

U.S. PATENT DOCUMENTS

| | | |
|---|---|---|
| 4,699,779 A | 10/1987 | Palinczar |
| 4,712,571 A | 12/1987 | Remz et al. |
| 4,724,137 A | 2/1988 | Hoppe et al. |
| 4,769,285 A | 9/1988 | Rasmussen |
| 4,806,338 A | 2/1989 | Smith |
| 4,806,345 A | 2/1989 | Bhattacharyya |
| 4,820,765 A | 4/1989 | Whyzmuzis |
| 4,822,601 A | 4/1989 | Goode et al. |
| 4,871,536 A | 10/1989 | Arraudeau et al. |
| 4,885,709 A | 12/1989 | Edgar et al. |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr |
| 5,073,364 A | 12/1991 | Giezendanner et al. |
| 5,085,859 A | 2/1992 | Halloran et al. |
| 5,102,656 A | 4/1992 | Kasat |
| 5,126,136 A | 6/1992 | Merat et al. |
| 5,166,355 A | 11/1992 | Leistner et al. |
| 5,186,318 A | 2/1993 | Oestreich et al. |
| 5,196,260 A | 3/1993 | Dirshl et al. |
| 5,223,559 A | 6/1993 | Arraudeau et al. |
| 5,237,071 A | 8/1993 | Leistner et al. |
| 5,252,323 A | 10/1993 | Richard et al. |
| 5,268,029 A | 12/1993 | Demangeon et al. |
| 5,272,241 A | 12/1993 | Lucarelli et al. |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,436,006 A | 7/1995 | Hirose et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Ross et al. |
| 5,505,937 A | 4/1996 | Castrogiovanni et al. |
| 5,510,452 A | 4/1996 | Santhanam |
| 5,534,247 A | 7/1996 | Franjac et al. |
| 5,536,871 A | 7/1996 | Santhanam |
| 5,538,718 A | 7/1996 | Aul et al. |
| 5,538,793 A | 7/1996 | Inokuchi et al. |
| 5,540,853 A | 7/1996 | Trinh et al. |
| 5,585,091 A | 12/1996 | Pelzer et al. |
| 5,603,925 A | 2/1997 | Ross et al. |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. |
| 5,679,357 A | 10/1997 | Dubief et al. |
| 5,683,817 A | 11/1997 | Kenmochi |
| 5,695,747 A | 12/1997 | Forestier et al. |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,795,565 A | 8/1998 | Eteve et al. |
| 5,800,816 A | 9/1998 | Brieva et al. |
| 5,807,968 A | 9/1998 | Heinrich et al. |
| 5,825,543 A | 10/1998 | Ouderkirk et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,849,909 A | 12/1998 | Richard et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. |
| 5,882,363 A | 3/1999 | Spaulding et al. |
| 5,891,424 A | 4/1999 | Bretzler et al. |
| 5,897,869 A | 4/1999 | Roulier et al. |
| 5,902,592 A | 5/1999 | Bara et al. |
| 5,908,631 A | 6/1999 | Arnaud et al. |
| 5,911,974 A | 6/1999 | Brieva et al. |
| 5,919,441 A | 7/1999 | Mendolia et al. |
| 5,925,337 A | 7/1999 | Arraudeau et al. |
| 5,945,095 A | 8/1999 | Mougin et al. |
| 5,945,112 A | 8/1999 | Flynn et al. |
| 5,955,060 A | 9/1999 | Huglin et al. |
| 5,959,009 A | 9/1999 | Konik et al. |
| 5,961,998 A | 10/1999 | Arnaud et al. |
| 5,962,452 A | 10/1999 | Haase et al. |
| 5,965,112 A | 10/1999 | Brieva et al. |
| 5,972,095 A | 10/1999 | Graves et al. |
| 5,972,354 A * | 10/1999 | de la Poterie et al. ...... 424/401 |
| 5,972,359 A | 10/1999 | Sine et al. |
| 5,976,512 A | 11/1999 | Huber |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A | 12/1999 | Pavlin et al. |
| 6,001,980 A | 12/1999 | Borzo et al. |
| 6,004,567 A | 12/1999 | Marchi-Lemann et al. |
| 6,007,796 A | 12/1999 | Menzel et al. |
| 6,007,799 A | 12/1999 | Lee et al. |
| 6,010,541 A | 1/2000 | de la Mettrie et al. |
| 6,019,962 A | 2/2000 | Rabe et al. |
| 6,036,947 A | 3/2000 | Barone et al. |
| 6,042,815 A | 3/2000 | Kellner et al. |
| 6,045,782 A | 4/2000 | Krog et al. |
| 6,045,823 A | 4/2000 | Vollhardt et al. |
| 6,051,216 A | 4/2000 | Barr et al. |
| 6,054,517 A | 4/2000 | Spaulding et al. |
| 6,060,072 A | 5/2000 | Konik et al. |
| 6,063,398 A | 5/2000 | Gueret |
| 6,066,328 A | 5/2000 | Ribier et al. |
| 6,074,654 A | 6/2000 | Drechsler et al. |
| 6,093,385 A | 7/2000 | Habeck et al. |
| 6,103,249 A | 8/2000 | Roulier et al. |
| 6,103,250 A | 8/2000 | Brieva et al. |
| 6,106,820 A | 8/2000 | Morrissey et al. |
| 6,111,055 A | 8/2000 | Berger et al. |
| 6,132,745 A | 10/2000 | Marchi-Lemann et al. |
| 6,156,325 A | 12/2000 | Farer et al. |
| 6,156,804 A | 12/2000 | Chevalier et al. |
| 6,159,455 A | 12/2000 | Habeck et al. |
| 6,165,454 A | 12/2000 | Patel et al. |
| 6,165,971 A | 12/2000 | Oppenlander et al. |
| 6,171,347 B1 | 1/2001 | Kunz |
| 6,177,523 B1 | 1/2001 | Reich et al. |
| 6,180,117 B1 | 1/2001 | Berthiaume et al. |
| 6,180,123 B1 | 1/2001 | Mondet |
| 6,190,673 B1 | 2/2001 | Guskey et al. |
| 6,197,100 B1 | 3/2001 | Melbouci |
| 6,203,780 B1 | 3/2001 | Arnaud et al. |
| 6,203,807 B1 | 3/2001 | Lemann |
| 6,214,326 B1 | 4/2001 | Dupuis |

| Patent No. | Date | Name |
|---|---|---|
| 6,214,329 B1 | 4/2001 | Brieva et al. |
| 6,221,389 B1 | 4/2001 | Cannell et al. |
| 6,224,851 B1 | 5/2001 | Bara |
| 6,242,509 B1 | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | de la Poterie et al. |
| 6,264,933 B1 | 7/2001 | Bodelin et al. |
| 6,268,466 B1 | 7/2001 | MacQueen et al. |
| 6,280,846 B1 | 8/2001 | Darby et al. |
| 6,287,552 B1 | 9/2001 | Tournilhac et al. |
| 6,299,979 B1 | 10/2001 | Neubauer et al. |
| 6,325,994 B1 | 12/2001 | Collin et al. |
| 6,348,563 B1 | 2/2002 | Fukuda et al. |
| 6,361,764 B2 | 3/2002 | Richard et al. |
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,387,498 B1 | 5/2002 | Coulter et al. |
| 6,399,080 B1 | 6/2002 | Bara |
| 6,399,081 B1 | 6/2002 | Nakanishi et al. |
| 6,402,408 B1 | 6/2002 | Ferrari |
| 6,410,003 B1 | 6/2002 | Bhatia et al. |
| 6,423,306 B2 | 7/2002 | Caes et al. |
| 6,423,324 B1 | 7/2002 | Murphy et al. |
| 6,428,773 B1 | 8/2002 | Oko et al. |
| 6,432,391 B1 | 8/2002 | Bara |
| 6,447,759 B2 | 9/2002 | Noguchi et al. |
| 6,469,131 B2 | 10/2002 | Lawson et al. |
| 6,475,500 B2 | 11/2002 | Vatter et al. |
| 6,479,686 B2 | 11/2002 | Nakanishi et al. |
| 6,482,400 B1 | 11/2002 | Collin |
| 6,489,283 B1 | 12/2002 | Afriat |
| 6,491,931 B1 | 12/2002 | Collin |
| 6,497,861 B1 | 12/2002 | Wang et al. |
| 6,503,521 B1 | 1/2003 | Atis et al. |
| 6,503,522 B2 | 1/2003 | Lawson et al. |
| 6,506,716 B1 | 1/2003 | Delplancke et al. |
| 6,545,174 B2 | 4/2003 | Habeck et al. |
| 6,552,160 B2 | 4/2003 | Pavlin |
| 6,607,734 B1 | 8/2003 | Afriat |
| 6,649,173 B1 | 11/2003 | Arnaud et al. |
| 6,656,487 B2 | 12/2003 | Afiat et al. |
| 6,682,748 B1 | 1/2004 | de la Poterie et al. |
| 6,689,345 B2 | 2/2004 | Jager Lezer |
| 6,716,420 B2 | 4/2004 | Feng et al. |
| 6,726,915 B2 | 4/2004 | Livoreil et al. |
| 6,726,917 B2 | 4/2004 | Kanji et al. |
| 6,761,881 B2 | 7/2004 | Bara |
| 6,830,610 B1 | 12/2004 | Bruchert et al. |
| 6,835,399 B2 * | 12/2004 | Collin .................. 424/707 |
| 6,869,594 B2 | 3/2005 | Ferrari |
| 6,875,245 B2 | 4/2005 | Pavlin |
| 6,881,400 B2 | 4/2005 | Collin |
| 6,960,339 B1 | 11/2005 | Ferrari et al. |
| 6,979,469 B2 | 12/2005 | Ferrari et al. |
| 7,144,582 B1 | 12/2006 | Ferrari et al. |
| 2001/0014312 A1 | 8/2001 | Nakanishi et al. |
| 2001/0014313 A1 | 8/2001 | Roulier et al. |
| 2001/0028887 A1 | 10/2001 | Douin et al. |
| 2001/0031280 A1 | 10/2001 | Ferrari et al. |
| 2001/0033846 A1 | 10/2001 | Roulier et al. |
| 2002/0010179 A1 | 1/2002 | Richard et al. |
| 2002/0044918 A1 | 4/2002 | Bara |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0107314 A1 | 8/2002 | Pinzon et al. |
| 2002/0111330 A1 | 8/2002 | Pinzon et al. |
| 2002/0114771 A1 | 8/2002 | Nakanishi |
| 2002/0114773 A1 | 8/2002 | Kanji et al. |
| 2002/0119171 A1 | 8/2002 | Gruning et al. |
| 2002/0120036 A1 | 8/2002 | Pinzon et al. |
| 2002/0122781 A1 | 9/2002 | Pinzon et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2002/0168335 A1 | 11/2002 | Collin |
| 2002/0172696 A1 | 11/2002 | Ferrari |
| 2002/0189030 A1 | 12/2002 | Collin |
| 2002/0192168 A1 | 12/2002 | Blin et al. |
| 2003/0012764 A1 | 1/2003 | Collin |
| 2003/0026772 A1 | 2/2003 | Jager-Lezer et al. |
| 2003/0044367 A1 | 3/2003 | Simon et al. |
| 2003/0086883 A1 | 5/2003 | Feng et al. |
| 2003/0129211 A9 | 7/2003 | Livoreil et al. |
| 2003/0147837 A1 | 8/2003 | Cavazzuti et al. |
| 2003/0161807 A1 | 8/2003 | Lemann |
| 2003/0161848 A1 | 8/2003 | Ferrari et al. |
| 2003/0185780 A1 | 10/2003 | Ferrari et al. |
| 2003/0198613 A1 | 10/2003 | Feng et al. |
| 2004/0013625 A1 | 1/2004 | Kanji |
| 2004/0028636 A1 | 2/2004 | Collin |
| 2004/0042980 A1 | 3/2004 | Kanji et al. |
| 2004/0086478 A1 | 5/2004 | Ferrari |
| 2004/0091510 A1 | 5/2004 | Feng et al. |
| 2004/0126401 A1 | 7/2004 | Collin |
| 2004/0156813 A2 | 8/2004 | Ferrari |
| 2004/0166076 A1 | 8/2004 | Ferrari et al. |
| 2004/0166133 A1 | 8/2004 | Cavazzuti et al. |
| 2004/0223987 A1 | 11/2004 | Ferrari |
| 2004/0247549 A1 | 12/2004 | Lu et al. |
| 2005/0008595 A1 | 1/2005 | Duffournier et al. |
| 2005/0008598 A1 | 1/2005 | Lu et al. |
| 2005/0008599 A1 | 1/2005 | Lu et al. |
| 2005/0065261 A1 | 3/2005 | Darlington, Jr. et al. |
| 2005/0089491 A1 | 4/2005 | Collin |
| 2005/0089505 A1 | 4/2005 | Collin |
| 2005/0089541 A1 | 4/2005 | Lacoutiere |
| 2005/0118122 A1 | 6/2005 | Simon et al. |
| 2005/0191327 A1 | 9/2005 | Yu et al. |
| 2006/0257336 A1 | 11/2006 | Ferrari et al. |

FOREIGN PATENT DOCUMENTS

| Country | Number | Date |
|---|---|---|
| CA | 1319306 | 6/1993 |
| DE | 38 39 136 A1 | 5/1990 |
| DE | 38 43 892 A1 | 6/1990 |
| DE | 42 08 297 A1 | 9/1993 |
| DE | 42 34 886 A1 | 4/1994 |
| DE | 195 43 988 A1 | 5/1997 |
| DE | 197 07 309 A1 | 8/1998 |
| DE | 197 26 184 A1 | 12/1998 |
| DE | 197 50 246 A1 | 5/1999 |
| DE | 197 55 649 A1 | 6/1999 |
| DE | 198 55 649 A1 | 6/2000 |
| DE | 199 51 010 A1 | 4/2001 |
| EP | 0 169 997 B1 | 2/1986 |
| EP | 0 295 886 B1 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 462 709 A2 | 12/1991 |
| EP | 0 507 692 A1 | 10/1992 |
| EP | 0 517 104 B1 | 12/1992 |
| EP | 0 518 772 A1 | 12/1992 |
| EP | 0 518 773 A1 | 12/1992 |
| EP | 0 557 196 A1 | 8/1993 |
| EP | 0 570 838 B1 | 11/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |

| | | | | | | |
|---|---|---|---|---|---|---|
| EP | 0 669 323 A1 | 8/1995 | | FR | 2 811 552 | 1/2002 |
| EP | 0 673 642 B1 | 9/1995 | | FR | 2 816 506 | 5/2002 |
| EP | 0 708 114 A1 | 4/1996 | | FR | 2 817 739 | 6/2002 |
| EP | 0 749 746 A1 | 12/1996 | | FR | 2 817 740 | 6/2002 |
| EP | 0 749 747 A1 | 12/1996 | | FR | 2 817 742 | 6/2002 |
| EP | 0 749 748 A1 | 12/1996 | | FR | 2 817 743 | 6/2002 |
| EP | 0 775 483 A1 | 5/1997 | | FR | 2 819 399 | 7/2002 |
| EP | 0 775 698 A1 | 5/1997 | | FR | 2 819 400 | 7/2002 |
| EP | 0 790 243 A1 | 8/1997 | | FR | 2 819 402 | 7/2002 |
| EP | 0 796 851 A1 | 9/1997 | | GB | 1 117 129 | 6/1968 |
| EP | 0 797 976 A2 | 10/1997 | | GB | 1 194 901 | 6/1970 |
| EP | 0 820 764 A1 | 1/1998 | | GB | 1 194 902 | 6/1970 |
| EP | 0 847 752 A1 | 6/1998 | | GB | 1 220 069 | 1/1971 |
| EP | 0 863 145 A2 | 9/1998 | | GB | 1 273 004 | 5/1972 |
| EP | 0 877 063 B1 | 11/1998 | | GB | 1 444 204 | 7/1976 |
| EP | 0 878 469 A1 | 11/1998 | | GB | 1 539 625 | 1/1979 |
| EP | 0 879 592 A2 | 11/1998 | | GB | 2 014 852 A | 9/1979 |
| EP | 0 887 073 A1 | 12/1998 | | GB | 2 021 411 A | 12/1979 |
| EP | 0 893 119 B1 | 1/1999 | | GB | 2 147 305 A | 5/1985 |
| EP | 0 923 928 A1 | 6/1999 | | GB | 2 196 978 A | 5/1988 |
| EP | 0 925 780 A1 | 6/1999 | | JP | 45-41318 | 12/1970 |
| EP | 0 928 608 A2 | 7/1999 | | JP | 48-38861 | 6/1973 |
| EP | 0 930 058 B1 | 7/1999 | | JP | 49-75740 | 7/1974 |
| EP | 0 930 060 A1 | 7/1999 | | JP | 50/58242 | 5/1975 |
| EP | 0 933 376 A2 | 8/1999 | | JP | 52-007067 | 1/1977 |
| EP | 0 943 340 A1 | 9/1999 | | JP | 53/043577 | 4/1978 |
| EP | 0 958 804 A2 | 11/1999 | | JP | 56/123909 | 9/1981 |
| EP | 0 958 805 A2 | 11/1999 | | JP | 56/166276 | 12/1981 |
| EP | 0 958 811 A1 | 11/1999 | | JP | 61/065809 | 4/1986 |
| EP | 0 959 066 A2 | 11/1999 | | JP | 62/061911 | 3/1987 |
| EP | 0 959 091 A1 | 11/1999 | | JP | 64-90110 | 4/1989 |
| EP | 0 967 200 A1 | 12/1999 | | JP | 2/127568 | 5/1990 |
| EP | 0 976 390 A1 | 2/2000 | | JP | 02/200612 | 8/1990 |
| EP | 0 984 025 A2 | 3/2000 | | JP | 02/207014 | 8/1990 |
| EP | 1 002 514 A1 | 5/2000 | | JP | 2/216279 | 8/1990 |
| EP | 1 018 332 | 7/2000 | | JP | 3/014683 | 1/1991 |
| EP | 1 031 342 A1 | 8/2000 | | JP | 04/346909 | 12/1992 |
| EP | 1 044 676 A2 | 10/2000 | | JP | 7/179795 | 7/1995 |
| EP | 1 048 282 A1 | 11/2000 | | JP | 7/267827 | 10/1995 |
| EP | 1 053 742 A1 | 11/2000 | | JP | 8/225316 | 9/1996 |
| EP | 1 062 944 A1 | 12/2000 | | JP | 9/20631 | 1/1997 |
| EP | 1 062 959 A1 | 12/2000 | | JP | 09/255560 | 9/1997 |
| EP | 1 064 919 A1 | 1/2001 | | JP | 9-263516 | 10/1997 |
| EP | 1 064 920 A1 | 1/2001 | | JP | 9/295922 | 11/1997 |
| EP | 1 066 814 A1 | 1/2001 | | JP | 10/001444 | 1/1998 |
| EP | 1 068 854 A1 | 1/2001 | | JP | 10/007527 | 1/1998 |
| EP | 1 068 855 A1 | 1/2001 | | JP | 10/120903 | 5/1998 |
| EP | 1 068 856 A1 | 1/2001 | | JP | 10/212213 | 8/1998 |
| EP | 1 086 945 A1 | 3/2001 | | JP | 10/259344 | 9/1998 |
| EP | 1 090 627 B1 | 4/2001 | | JP | 11/106216 | 4/1999 |
| EP | 1 095 959 A2 | 5/2001 | | JP | 11/335228 | 12/1999 |
| EP | 1 114 636 A1 | 7/2001 | | JP | 11/335242 | 12/1999 |
| EP | 1 213 011 A1 | 6/2002 | | JP | 11/335254 | 12/1999 |
| EP | 1 213 316 A2 | 6/2002 | | JP | 2000038314 A | 2/2000 |
| FR | 1 529 329 | 5/1968 | | JP | 2000038316 A | 2/2000 |
| FR | 2 232 303 | 1/1975 | | JP | 2000038317 A | 2/2000 |
| FR | 2 315 991 | 1/1977 | | JP | 2000038321 A | 2/2000 |
| FR | 2 416 008 | 8/1979 | | JP | 2000/503305 | 3/2000 |
| FR | 2 674 126 | 9/1992 | | JP | 2000086427 A | 3/2000 |
| FR | 2 785 179 | 5/2000 | | JP | 2000086429 A | 3/2000 |
| FR | 2 796 270 | 1/2001 | | JP | 2000086438 A | 3/2000 |
| FR | 2 796 271 | 1/2001 | | JP | 2000/0154112 | 6/2000 |
| FR | 2 796 272 | 1/2001 | | JP | 2002-539220 | 11/2002 |
| FR | 2 796 273 | 1/2001 | | WO | WO 86/04916 | 8/1986 |
| FR | 2 796 276 | 1/2001 | | WO | WO 87/03783 | 7/1987 |
| FR | 2 796 550 | 1/2001 | | WO | WO 91/12793 | 9/1991 |
| FR | 2 802 806 | 6/2001 | | WO | WO 93/04665 | 3/1993 |
| FR | 2 804 014 | 7/2001 | | WO | WO 93/21763 | 11/1993 |
| FR | 2 804 017 | 7/2001 | | WO | WO 93/23008 | 11/1993 |
| FR | 2 804 018 | 7/2001 | | WO | WO 94/18261 | 8/1994 |
| FR | 2 804 286 | 8/2001 | | WO | WO 94/21233 | 9/1994 |
| FR | 2 810 562 | 12/2001 | | WO | WO 95/15741 | 6/1995 |
| FR | 2 811 225 | 1/2002 | | WO | WO 95/24887 | 9/1995 |

| WO | WO 95/33000 | 12/1995 |
| WO | WO 96/15761 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/25922 | 6/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 99/36477 | 7/1999 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 A1 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47606 A2 | 6/2002 |
| WO | WO 02/47608 A2 | 6/2002 |
| WO | WO 02/47619 A2 | 6/2002 |
| WO | WO 02/47620 A2 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 A2 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |
| WO | WO 2005/013887 A2 | 2/2005 |

OTHER PUBLICATIONS

English language Derwent abstract for JP 48-38861.
English language Derwent abstract for JP 64-90110.
English language Derwent abstract for JP 45-41318.
English language esp@cenet abstract for JP 52-007067.
English language esp@cenet abstract for JP 10/001444.
Co-pending U.S. Appl. No. 11/312,338, Title: Composition and Process for Coating Keratin Fibers, U.S. Filing Date Dec. 21, 2005.
Co-Pending U.S. Appl. No. 11/351,309, Title: Cosmetic Composition Containing a Polymer and a Fluoro Oil, U.S. Filing Feb. 10, 2006.
Co-Pending U.S. Appl. No. 11/406,371, Title: Cosmetic Composition Comprising Silica Particles, Reflecting Particles, and at Least One Polymer, Preparative Process, and Uses Thereof, U.S. Filing Apr. 19, 2006.
Estee Lauder's Answer and Counterclaims, dated May 27, 2004, in the on-going litigation *L'Oreal S.A., et al., v. The Estee Lauder Companies Inc., et al.*, Civil Action No. 04-1660 (D.N.J.).
L'Oreal's Complaint for Patent Infringement, dated Apr. 7, 2004, in the on-going litigation *L'Oreal S.A., et al., v. The Estee Lauder Companies Inc.*, et al., Civil Action No. 04-1660 (D.N.J.).

Office Action in co-pending U.S. Appl. No. 09/733,896 dated Jan. 30, 2006.
Office Action in co-pending U.S. Appl. No. 09/733,897 dated Feb. 8, 2006.
Office Action in co-pending U.S. Appl. No. 09/733,898 dated Jan. 11, 2006.
Office Action in co-pending U.S. Appl. No. 10/047,987 dated Sep. 7, 2004.
Office Action in co-pending U.S. Appl. No. 10/129,377 dated Jan. 13, 2006.
Office Action in co-pending U.S. Appl. No. 10/182,830 dated Nov. 25, 2005.
Office Action in co-pending U.S. Appl. No. 10/203,254 dated Dec. 5, 2005.
Office Action in co-pending U.S. Appl. No. 10/312,083 dated Apr. 6, 2006.
Office Action in co-pending U.S. Appl. No. 10/746,612 dated Feb. 17, 2006.
Office Action in co-pending U.S. Appl. No. 11/212,811 dated Nov. 17, 2005.
Richard J. Lewis, Sr., "Fatty Acid," Hawley's Condensed Chemical Dictionary 487 (13th ed., 1997).
A. D. Bangham et al.. Diffusion of Univalent Ions across the Lamellae of Swollen Phospholipids, Journal of Molecular Biology, pp. 238-252, vol. 13, Aug. to Oct. 1965.
Bush Boake Allen, Inc., Uniclear Formulations, dated Oct. 13, 1998.
Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104-117.
Co-Pending U.S. Appl. No. 11/312,338, Title: Composition and Process for Coating Keratin Fibers, filed Dec. 21, 2005.
Co-Pending U.S. Appl. No. 09/618,032; issued as U.S. Patent No. 6,402,408 on Jun. 11, 2002, Title: Composition Containing a Liquid Fatty Phase Gelled with a Polyamide Containing Ester End Groups Inventor: Véronique Ferrari, filed Jul. 17, 2000.
Co-Pending U.S. Appl. No. 09/618,066; Title: Compositions in Rigid form Structured with a Polymer Inventors: Véronique Ferrari and Pascal Simon, filed Jul. 17, 2000.
Co-Pending U.S. Appl. No. 09/685,577; Title: Compositions in Rigid Form Structured with a Polymer Inventors: Véronique Ferrari and Pascal Simon, filed Oct. 11, 2000.
Co-Pending U.S. Appl. No. 09/685,578, Title: Composition Containing a Liquid Fatty Phase Gelled with A Polyamide Containing Ester End Groups Inventor: Véronique Ferrari, filed CIP filed Oct. 11, 2000.
Co-Pending U.S. Appl. No. 09/733,896; Title Compositions Containing Heteropolymers and Oil-Soluble Polymers and Methods of Using Same Inventors: Carlos Pinzon and Paul Thau, filed Dec. 12, 2000.
Co-Pending U.S. Appl. No. 09/733,897; Title: Compositions Containing Heteropolymers and Methods of Using Same Inventors: Carlos Pinzon and Paul Thau, filed Dec. 12, 2000.
Co-Pending U.S. Appl. No. 09/733,898; Title: Compositions Containing Heteropolymers and Oil-Soluble Esters and Methods of Using Same Inventors: Carlos Pinzon and Paul Thau, filed Dec. 12, 2000.
Co-Pending U.S. Appl. No. 09/733,899; Title: Cosmetic Compositions Containing at Least one Hetero Polymer and at Least one Film-Forming Silicone Resin and Methods of Using Inventors: Mohamed Kanji et al., filed Dec. 12, 2000.
Co-Pending U.S. Appl. No. 09/733,900; Title: Cosmetic Compositions Containing Heteropolymers and Oil-Soluble Cationic Surfactants and Methods of Using Inventors: Carlos Pinzon and Paul Thau, filed Dec. 12, 2000.
Co-Pending U.S. Appl. No. 09/749,036; Title: Composition Comprising at Least One Hetero Polymer and at Least One Pasty Fatty Substance and Methods for Use Inventors: Véronique Ferrari et al., filed Dec. 28, 2000.
Co-Pending U.S. Appl. No. 09/937,314; Title: Transfer-Free Composition Structured in the Stiff Form by a Polymer, filed Sep. 24, 2001.

Co-Pending U.S. Appl. No. 10/012,029; Title: Cosmetic Composition Comprising a Polymer Blend, filed Dec. 11, 2001.
Co-Pending U.S. Appl. No. 10/012,051; Title: Use of a Polymer for Obtaining an Express Make-Up of Keratin Materials, filed Dec. 11, 2001.
Co-Pending U.S. Appl. No. 10/012,052; Title: Cosmetic Composition Comprising a Wax and a Polymer, filed Dec. 11, 2001.
Co-Pending U.S. Appl. No. 10/046,568; Title: Nail Polish Composition Comprising a Polymer, filed Jan. 16, 2002.
Co-Pending U.S. Appl. No. 10/047,987, Title: Cosmetic Composition Containing a Polymer and a Fluoro Oil U.S., filed Jan. 17, 2002.
Co-Pending U.S. Appl. No. 10/129,377; Title: Compositions Structured with a Polymer Containing A Heteroatom and an Organogelator, filed May 3, 2002.
Co-Pending U.S. Appl. No. 10/182,830; Title: Cosmetic Composition Comprising Hetero Polymers and a Solid Substance and Method of Using Same, filed Aug. 2, 2002.
Co-Pending U.S. Appl. No. 10/198,931, Title: Compositions Comprising at Least One Heteropolymer and Fibers, and Methods of Using the Same, filed Jul. 22, 2002.
Co-Pending U.S. Appl. No. 10/203,018; Title: Composition Comprising at Least One Hetero Polymer and at Least One Inert Filler and Methods for Use, filed Aug. 5, 2002.
Co-Pending U.S. Appl. No. 10/203,254; Title: Cosmetic Compositions Containing at Least One Heteropolymer and at Least One Gelling Agent and Methods of Using the Same, filed Aug. 7, 2002.
Co-Pending U.S. Appl. No. 10/203,374; Title: Method for Making a Coloured Make-Up Cosmetic Composition With Controlled Transmittance, filed Aug. 9, 2002.
Co-Pending U.S. Appl. No. 10/203,375, Title: Transparent or Translucent Colored Cosmetic Composition, filed Aug. 9, 2002.
Co-Pending U.S. Appl. No. 10/312,083, Title: Solid Emulsion Containing a Liquid Fatty Phase Structured With a Polymer, filed Dec. 23, 2002.
Co-Pending U.S. Appl. No. 10/413,217, Title: Methods of Dispersing at Least One Coloring Agent Using at Least One Heteropolymer, filed Apr. 15, 2003.
Co-Pending U.S. Appl. No. 10/450,108, Title: Cosmetic Composition Comprising a Polymer and Fibres, filed Jun. 11, 2003.
Co-Pending U.S. Appl. No. 10/459,636, Title: Cosmetic Emulsions Containing at Least One Hetero Polymer and at Least One Sunscreen and Methods of Using the Same, filed Jun. 12, 2003.
Co-Pending U.S. Appl. No. 10/466,166, Title: Cosmetic Composition Comprising a Mixture of Polymers, filed Jul. 14, 2003.
Co-Pending U.S. Appl. No. 10/494,864; Title: Composition Containing an Amino Acid N-Acylated Ester and a Polyamide-Structured UV Filter, filed Nov. 23, 2004.
Co-Pending U.S. Appl. No. 10/618,315, Title: Cosmetic Compositions Comprising a Structuring Agent, Silicone Powder and Swelling Agent, filed Jul. 11, 2003.
Co-Pending U.S. Appl. No. 10/699,780, Title: Methods of Dispersing at Least One Coloring Agent Using at Least One Heteropolymer, filed Nov. 4, 2003.
Co-Pending U.S. Appl. No. 10/746,612, Title: Cosmetic Compositions Comprising a Structuring Agent, Silicone Powder and Swelling Agent, filed Dec. 22, 2003.
Co-Pending U.S. Appl. No. 10/747,412, Title: Cosmetic Emulsions Containing at Least One Hetero Polymer and at Least One Sunscreen and Methods of Using the Same, filed Dec. 22, 2003.
Co-Pending U.S. Appl. No. 10/787,440, Title: Composition Comprising at Least One Hetero Polymer and at Least One Inert Filler and Methods for Use, filed Feb. 27, 2004.
Co-Pending U.S. Appl. No. 10/787,441, Title: Cosmetic Composition Comprising Hetero Polymers and a Solid Substance and Method of Using Same, filed Feb. 27, 2004.
Co-Pending U.S. Appl. No. 10/918,579, Title: Compositions Containing Heteropolymers and Oilsoluble Esters and Methods of Using Same, filed Aug. 16, 2004.
Co-Pending U.S. Appl. No. 10/990,475, Title: Use of a Polymer for Obtaining an Express Make-Up of Keratin Materials, filed Nov. 18, 2004.
Co-Pending U.S. Appl. No. 10/993,431, Title: A Transfer-Free Composition Structured in Rigid Form by a Polymer, filed Nov. 22, 2004.
Co-Pending U.S. Appl. No. 11/019,382, Title: Cosmetic Composition Comprising Two Different Hetero Polymers and Method of Using Same, filed Dec. 23, 2004.
Co-Pending U.S. Appl. No. 11/212,811, Title: A Transfer-Free Mascara Composition Comprising at Least One Volatile Solvent and at Least One Polymer, filed Aug. 29, 2005.
English Language Abstract of FR 2 804 014 from esp@cenet.
English Language Abstract of FR 2 817 742 from esp@cenet.
English language abstract of JP 02/207014 from Patent Abstracts of Japan.
English language abstract of JP 53/043577 from Patent Abstracts of Japan.
English language abstract of JP 56/123909 from Patent Abstracts of Japan.
English language abstract of JP 56/166276 from Patent Abstracts of Japan.
English language abstract of JP 78/043577.
English language DERWENT abstract of DE 195 43 988 A1.
English language DERWENT abstract of DE 197 07 309 A1.
English language DERWENT abstract of DE 197 26 184 A1.
English language DERWENT abstract of DE 197 50 246 A1.
English language DERWENT abstract of DE 197 55 649 A1.
English language DERWENT abstract of DE 198 55 649 A1.
English language DERWENT abstract of DE 199 51 010 A1.
English language DERWENT abstract of DE 38 39 136 A1.
English language DERWENT abstract of DE 38 43 892 A1.
English language DERWENT abstract of DE 42 08 297 A1.
English language DERWENT abstract of DE 42 34 886 A1.
English language DERWENT abstract of EP 0 169 997 B1.
English language DERWENT abstract of EP 0 507 692 A1.
English language DERWENT abstract of EP 0 518 772 A1.
English language DERWENT abstract of EP 0 518 773 A1.
English language DERWENT abstract of EP 0 557 196 A1.
English language DERWENT abstract of EP 0 609 132 B1.
English language DERWENT abstract of EP 0 669 323 A1.
English language DERWENT abstract of EP 0 749 746 A1.
English language DERWENT abstract of EP 0 749 747 A1.
English language DERWENT abstract of EP 0 749 748 A1.
English language DERWENT abstract of EP 0 775 483 A1.
English language DERWENT abstract of EP 0 775 698 A1.
English language DERWENT abstract of EP 0 790 243 A1.
English language DERWENT abstract of EP 0 820 764 A1.
English language DERWENT abstract of EP 0 847 752 A1.
English language DERWENT abstract of EP 0 863 145 A2.
English language DERWENT abstract of EP 0 878 469 A1.
English language DERWENT abstract of EP 0 879 592 A2.
English language DERWENT abstract of EP 0 887 073 A1.
English language DERWENT abstract of EP 0 923 928 A1.
English language DERWENT abstract of EP 0 925 780 A1.
English language DERWENT abstract of EP 0 930 058 B1.
English language DERWENT abstract of EP 0 930 060 A1.
English language DERWENT abstract of EP 0 943 340 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 967 200 A1.
English language DERWENT abstract of EP 0 976 390 A1.
English language DERWENT abstract of EP 1 002 514 A1.
English language DERWENT abstract of EP 1 031 342 A1.
English language DERWENT abstract of EP 1 048 282 A1.
English language DERWENT abstract of EP 1 053 742 A1.
English language DERWENT abstract of EP 1 064 919 A1.
English language DERWENT abstract of EP 1 064 920 A1.
English language DERWENT abstract of EP 1 066 814 A1.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of EP 1 114 636 A1.

English language DERWENT abstract of FR 2 232 303.
English language DERWENT abstract of FR 2 315 991.
English language DERWENT abstract of FR 2 416 008.
English language DERWENT abstract of FR 2 674 126.
English language DERWENT abstract of FR 2 785 179.
English language DERWENT abstract of FR 2 796 270.
English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 796 550.
English language DERWENT abstract of FR 2 802 806.
English language DERWENT abstract of FR 2 804 017.
English language DERWENT abstract of FR 2 804 018.
English language DERWENT abstract of FR 2 810 562.
English language DERWENT abstract of FR 2 811 225.
English language DERWENT abstract of FR 2 811 552.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 02/200612.
English language DERWENT abstract of JP 04/346909.
English language DERWENT abstract of JP 09/255560.
English language DERWENT abstract of JP 10/007527.
English language DERWENT abstract of JP 10/120903.
English language DERWENT abstract of JP 10/212213.
English language DERWENT abstract of JP 10/259344.
English language DERWENT abstract of JP 11/106216.
English language DERWENT abstract of JP 11/335228.
English language DERWENT abstract of JP 11/335242.
English language DERWENT abstract of JP 11/335254.
English language DERWENT abstract of JP 2/127568.
English language DERWENT abstract of JP 2/216279.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.
English language DERWENT abstract of JP 3014683.
English language DERWENT abstract of JP 61065809.
English language DERWENT abstract of JP 62061911.
English language DERWENT abstract of JP 7179795.
English language DERWENT abstract of JP 7267827.
English language DERWENT abstract of JP 8225316.
English language DERWENT abstract of JP 920631.
English language DERWENT abstract of JP 9295922.
English language DERWENT abstract of WO 01/97773 A1.
English language DERWENT abstract of WO 02/056847 A1.
English language DERWENT abstract of WO 02/056848 A1.
English language DERWENT abstract of WO 02/47622 A2.
English language DERWENT abstract of WO 02/47629 A1.
English language DERWENT abstract of WO 02/47630 A1.
English language DERWENT abstract of WO 86/04916.
English language DERWENT abstract of WO 93/04665.
English language DERWENT abstract of WO 98/25922.
Estee Lauder MagnaScopic Maximum Volume mascara product packaging, believed to have first been sold in 2003.
Estee Lauder's Amended Answer and Counterclaims, dated Apr. 21, 2005, in the on-going litigation L'Oreal S.A., et al., v. The Estee Lauder Companies Inc., et al, Civil Action No. 04-1660 (D.N.J.).
Estee Lauder's Response to Plaintiff's First Set of Interrogatories (Nos. 1-6), dated Sep. 27, 2004, in the on-going litigation L'Oreal S.A., et al. v. The Estee Lauder Companies Inc., et al., Civil Action No. 04-1660 (D.N.J.).
Estee Lauder's Response to Plaintiff's Third Set of Interrogatories (Nos. 8-13), dated Jun. 21, 2005, in the on-going litigation L'Oreal S.A. et al., v. The Estee Lauder Companies Inc., et al., Civil Action No. 04-1660 (D.N.J.).
French Search Report in FR 0000920, dated Nov. 10, 2000.
French Search Report in FR 0001004, dated Nov. 10, 2000.
French Search Report in FR 0008084, dated Mar. 28, 2001.
French Search Report in FR 0008913, dated Mar. 20, 2001.
French Search Report in FR 0016161, dated Sep. 6, 2001.
French Search Report in FR 0016163, dated Aug. 1, 2001.
French Search Report in FR 0016164, dated Sep. 6, 2001.
French Search Report in FR 0016180, dated Oct. 16, 2001.
French Search Report in FR 0100479, dated Sep. 17, 2001.
French Search Report in FR 0100620, dated Nov. 6, 2001.
French Search Report in FR 0100623, dated Oct. 9, 2001.
French Search Report in FR 0114529, dated Aug. 26, 2002.
French Search Report in FR 0114530, dated Aug. 26, 2002.
French Search Report in FR 9909176, dated Mar. 23, 2000.
French Search Report in FR 9909177, dated Mar. 30, 2000.
French Search Report in FR 9916588, dated Oct. 16, 2000.
Handbook of Cosmetic Science and Tech. Elsevier Advanced Tech., 1st Edition (1994), pp. 1-32.
Harry's Cosmeticology 375-383 (J.B. Wilkinson & R.J. Moore eds., Chemical Pub. 7th ed. 1982).
International Search Report in PCT/FR01/00229, dated Apr. 18, 2001.
International Search Report in PCT/FR01/01958, dated Oct. 26, 2001.
International Search Report in PCT/FR01/03726, dated Apr. 18, 2002.
International Search Report in PCT/FR01/03937, dated Apr. 23, 2002.
International Search Report in PCT/FR01/03938, dated Jun. 10, 2002.
International Search Report in PCT/FR01/03939, (priority document for FR 0016164), dated Apr. 15, 2002.
International Search Report in PCT/FR01/03940, (priority document for FR 0016161), dated Mar. 13, 2002.
International Search Report in PCT/FR01/03945, (priority document for FR 0016163), dated May 31, 2002.
International Search Report in PCT/FR02/00129, dated Jun. 14, 2002.
International Search Report in PCT/FR02/00144 (priority document for FR 0100479), dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Oct. 4, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US00/33596, dated Aug. 8, 2001.
International Search Report in PCT/US01/47454, dated Aug. 29, 2002.
International Search Report in PCT/US01/47459, dated Feb. 6, 2003.
International Search Report in PCT/US01/47496, dated Feb. 26, 2003.
International Search Report in PCT/US01/47497, dated Dec. 2, 2002.
International Search Report in PCT/US01/47499, dated Aug. 8, 2002.
International Search Report in PCT/US03/41618, dated Mar. 11, 2005.

International Search Report in PCT/US04/01071, dated Feb. 22, 2005.

Kenji Hanabusa et al., Easy Preparation and Prominent Gelation of New Gelator Based on L-Lysine, 2000 Chem. Letters, 1070-1071.

Kenji Hanabusa et al., Prominent Gelation and Chiral Aggregation of Alkylamides Derived from trans-1,2-Diaminocyclohexane, Angew. Chem. Int. Ed. Engl. 1996, 35, No. 17, 1949-1951.

Kenji Hanabusa et al., Terephthaloyl Derivatives as New Gelators; Excellent Gelation Ability and Remarkable Increase of Gel Strength by Adding Polymers, 1999 Chemistry Letters 767-768.

Kirk-Othmer, "Encyclopedia of Chemical Technology", Third Edition, vol. 22, John Wiley & Sons, 1983, pp. 332-342.

McCutcheon's vol. 1: Emulsifiers & Detergents, North American Edition MC Publishing Co., Glen Rock NJ (1993), pp. 272-273.

Milan Jokic et al., A Novel Type of Small Organic Gelators: Bis(Amino Acid) Oxalyl Amides, 1995 J. Chem. Soc., Chem. Commun., 1723-1724.

Office Action in co-pending U.S. Appl. No. 09/618,066, filed Dec. 21, 2001.
Office Action in co-pending U.S. Appl. No. 09/618,066, filed Jul. 15, 2002.
Office Action in co-pending U.S. Appl. No. 09/618,066, filed Jul. 16, 2003.
Office Action in co-pending U.S. Appl. No. 09/618,066, filed Nov. 19, 2003.
Office Action in co-pending U.S. Appl. No. 09/685,577, filed Aug. 11, 2004.
Office Action in co-pending U.S. Appl. No. 09/685,577, filed Jul. 15, 2002.
Office Action in co-pending U.S. Appl. No. 09/685,577, filed Jul. 16, 2003.
Office Action in co-pending U.S. Appl. No. 09/685,577, filed Nov. 19, 2003.
Office Action in co-pending U.S. Appl. No. 09/685,578, filed Aug. 11, 2004.
Office Action in co-pending U.S. Appl. No. 09/685,578, filed Feb. 8, 2005.
Office Action in co-pending U.S. Appl. No. 09/685,578, filed May 7, 2003.
Office Action in co-pending U.S. Appl. No. 09/685,578, filed Nov. 19, 2003.
Office Action in co-pending U.S. Appl. No. 09/733,896, filed Jan. 28, 2003.
Office Action in co-pending U.S. Appl. No. 09/733,896, filed Jul. 13, 2005.
Office Action in co-pending U.S. Appl. No. 09/733,896, filed Jul. 19, 2002.
Office Action in co-pending U.S. Appl. No. 09/733,896, filed Nov. 18, 2003.
Office Action in co-pending U.S. Appl. No. 09/733,897, filed Apr. 15, 2002.
Office Action in co-pending U.S. Appl. No. 09/733,897, filed Apr. 23, 2003.
Office Action in co-pending U.S. Appl. No. 09/733,897, filed Aug. 29, 2002.
Office Action in co-pending U.S. Appl. No. 09/733,897, filed May 6, 2004.
Office Action in co-pending U.S. Appl. No. 09/733,898, filed Apr. 25, 2005.
Office Action in co-pending U.S. Appl. No. 09/733,898, filed Apr. 29, 2003.
Office Action in co-pending U.S. Appl. No. 09/733,898, filed Aug. 28, 2002.
Office Action in co-pending U.S. Appl. No. 09/733,898, filed Dec. 23, 2003.
Office Action in co-pending U.S. Appl. No. 09/733,899, filed Apr. 7, 2004.
Office Action in co-pending U.S. Appl. No. 09/733,899, filed Apr. 9, 2003.
Office Action in co-pending U.S. Appl. No. 09/733,899, filed May 3, 2005.
Office Action in co-pending U.S. Appl. No. 09/733,899, filed Sep. 22, 2004.
Office Action in co-pending U.S. Appl. No. 09/733,900, filed Apr. 7, 2004.
Office Action in co-pending U.S. Appl. No. 09/733,900, filed Dec. 1, 2004.
Office Action in co-pending U.S. Appl. No. 09/733,900, filed Jul. 16, 2003.
Office Action in co-pending U.S. Appl. No. 09/733,900, filed Jun. 2, 2005.
Office Action in co-pending U.S. Appl. No. 09/749,036, filed Aug. 13, 2003.
Office Action in co-pending U.S. Appl. No. 09/749,036, filed Jul. 16, 2002.
Office Action in co-pending U.S. Appl. No. 09/749,036, filed May 5, 2004.
Office Action in co-pending U.S. Appl. No. 09/749,036, filed Apr. 29, 2005.
Office Action in co-pending U.S. Appl. No. 09/749,036, filed Nov. 23, 2005.
Office Action in co-pending U.S. Appl. No. 09/899,909, filed Dec. 18, 2001.
Office Action in co-pending U.S. Appl. No. 09/937,314, filed May 19, 2004.
Office Action in co-pending U.S. Appl. No. 09/971,028, filed Aug. 11, 2003.
Office Action in co-pending U.S. Appl. No. 09/971,028, filed Mar. 26, 2003.
Office Action in co-pending U.S. Appl. No. 10/012,029, filed Nov. 20, 2002.
Office Action in co-pending U.S. Appl. No. 10/012,029, filed Sep. 8, 2003.
Office Action in co-pending U.S. Appl. No. 10/012,051, filed Jan. 14, 2003.
Office Action in co-pending U.S. Appl. No. 10/012,051, filed May 14, 2004.
Office Action in co-pending U.S. Appl. No. 10/012,051, filed Oct. 3, 2003.
Office Action in co-pending U.S. Appl. No. 10/012,052, filed Aug. 9, 2004.
Office Action in co-pending U.S. Appl. No. 10/012,052, filed Nov. 6, 2003.
Office Action in co-pending U.S. Appl. No. 10/012,052, filed Jun. 3, 2005.
Office Action in co-pending U.S. Appl. No. 10/046,568, filed Dec. 30, 2003.
Office Action in co-pending U.S. Appl. No. 10/046,568, filed Jun. 12, 2003.
Office Action in co-pending U.S. Appl. No. 10/046,568, filed Nov. 5, 2002.
Office Action in co-pending U.S. Appl. No. 10/046,568, filed Sep. 22, 2004.
Office Action in co-pending U.S. Appl. No. 10/047,987, filed Dec. 11, 2003.
Office Action in co-pending U.S. Appl. No. 10/047,987, filed Sep. 7, 2004.
Office Action in co-pending U.S. Appl. No. 10/182,830, filed Apr. 4, 2005.
Office Action in co-pending U.S. Appl. No. 10/182,830, filed Aug. 24, 2004.
Office Action in co-pending U.S. Appl. No. 10/198,931, filed Dec. 18, 2003.
Office Action in co-pending U.S. Appl. No. 10/198,931, filed Sep. 1, 2004.
Office Action in co-pending U.S. Appl. No. 10/203,018, filed May 19, 2004.
Office Action in co-pending U.S. Appl. No. 10/203,254, filed Apr. 22, 2005.
Office Action in co-pending U.S. Appl. No. 10/203,375, filed May 13, 2005.

Office Action in co-pending U.S. Appl. No. 10/312,083, filed Apr. 18, 2005.
Office Action in co-pending U.S. Appl. No. 10/312,083, filed Oct. 1, 2004.
Office Action in co-pending U.S. Appl. No. 10/312,083, filed Sep. 28, 2005.
Office Action in co-pending U.S. Appl. No. 10/413,217, filed Sep. 9, 2004.
Office Action in co-pending U.S. Appl. No. 10/699,780, filed Sep. 22, 2004.
Office Action in co-pending U.S. Appl. No. 10/699,780, filed Jun. 15, 2005.
Office Action in co-pending U.S. Appl. No. 10/746,612, filed Sep. 20, 2004.
Office Action in co-pending U.S. Appl. No. 10/746,612, filed Jun. 15, 2005.
Office Action in co-pending U.S. Appl. No. 10/787,440, filed Aug. 24, 2004.
Office Action in co-pending U.S. Appl. No. 10/787,441, filed Apr. 5, 2005.
Office Action in co-pending U.S. Appl. No. 10/990,475, filed Nov. 2, 2005.
Office Action in co-pending U.S. Appl. No. 11/212,811, filed Nov. 17, 2005.
Origins Full Story™ Lush lash mascara product packaging, believed to have first been sold in 2003.
P. Terech, "Low-Molecular Weight Organogelators," in Specialist Surfactants, ch. 8, pp. 208-268 (I.D. Robb, ed., 1997).
Partial International Search Report in PCT/US 01/47497, dated Nov. 15, 2002.
PCT Application No. PCT/FR01/03962; Title: Composition Comprising at Least One Heteropolymer and at Least One Inert Filler and Methods for Use Inventors: Véronique Ferrari et al. International Filing Date: Dec. 12, 2001.
PCT Application No. PCT/FR01/03963; Title: Cosmetic Compositions Containing at Least One Heteropolymer and at Least One Gelling Agent and Methods of Using the Same Inventor: Véronique Ferrari International Filing Date: Dec. 12, 2001.
PCT Application No. PCT/FR01/03965; Title: Cosmetic Composition Comprising Hetero Polymers and a Solid Substance and Method of Using Same Inventors: Roberto Cavazzuti et al. International Filing Date: Dec. 12, 2001.
PCT Application No. PCT/IB00/02000; Title: Composition Comprising at Least One Hetero Polymer and at Least One Inert Filler and Methods for Use Inventors: Véronique Ferrari et al. International Filing Date: Dec. 12, 2000.
PCT Application No. PCT/IB00/02006; Title: Cosmetic Compositions Containing at Least One Heteropolymer and at Least One Gelling Agent and Methods of Using the Same Inventor: Véronique Ferrari International Filing Date:Dec. 12, 2000.
PCT Application No. PCT/IB01/02780; Title:Composition Structured With a Polymer Containing a Heteroatom Organogelator International Filing Date: Dec. 12, 2001.
PCT Application No. PCT/US00/33596; Title Cosmetic Composition Comprising Hetero Polymers and a Solid Substance and Method of Using Same Inventors: Roberto Cavazzuti et al. International Filing Date: Dec. 12, 2000.
PCT Application No. PCT/US01/47454; Title: Compositions Containing Heteropolymers and Oil-Soluble Polymers and Methods of Using Same Inventors: Carlos Pinzon and Paul Thau U.S. Filing Date: Dec. 12, 2001.
PCT Application No. PCT/US01/47459; Title: Cosmetic Compositions Containing at Least One Hetero Polymer and Least One Film-Forming Silicone Resin and Methods of Using Inventors: Mohamed Kanji et al. U.S. Filing Date:Dec. 12, 2001.
PCT Application No. PCT/US01/47496; Title: Compositions Containing Heteropolymers and Methods of Using Same Inventors: Carlos Pinzon and Paul Thau U.S. Filing Date: Dec. 12, 2001.
PCT Application No. PCT/US01/47497; Title: Compositions Containing Heteropolymers and Oil-Soluble Esters and Methods of Using Same Inventors: Carlos Pinzon and Paul Thau U.S. Filing Date: Dec. 12, 2001.
PCT Application No. PCT/US01/47499; Title Cosmetic Compositions Containing Heteropolymers and Oil-Soluble Cationic Surfactants and Methods of Using Same Inventors: Carlos Pinzon and Paul Thau U.S. Filing Date: Dec. 12, 2001.
PCT Application No. PCT/US03/41618; Title: Cosmetic Compositions Comprising a Structuring Agent, Silicone Powder and Swelling Agent Inventors: Shao Xiang Lu, Terry Van Liew, Nathalie Geffroy-Hyland International Filing Date: Dec. 22, 2003.
PCT Application No. PCT/US04/01071: Title; Long Wear Cosmetic Composition Inventor: Balanda ATIS International Filing Date: Jan. 16, 2004.
Richard J. Lewis, Sr., "Ricinoleic Acid," Hawley's Condensed Chemical Dictionary 972 (13th. 1997).
Toshimi Shimizu et al., Stereochemical Effect of Even-Odd Connecting Links on Supramolecular Assemblies Made of 1-Glucosamide Bolaamphiphiles, J. Am Chem. Soc. 1997, 119, 2812-2818.
U.S. District Court for the District of New Jersey Civil Docket for *L'Oreal S.A. et al. v. Estee Lauder Companies, Inc., et al.*, Civ. No. 04-1660 (HAA) (filed Apr. 7, 2004) (retrieved Jan. 2, 2005).
Xuzhong Luo et al., Self-assembled organogels formed by monoalkyl derivatives of oxamide, 2000 Chem. Commun. 2091-92.
Yasuda et al., Novel Low-molecular-weight Organic Gels: N,N', N"-Tristearyltrimesamide/Organic Solvent System," Chemistry Letters, pp. 575-576, 1996, the month of publication is not available.
English language Abstract from Patent Abstracts of Japan for JP 2000/0154112.
English language DERWENT abstract of FR 2,804,286.
Office Action in co-pending U.S. Appl. No. 09/733,897, filed Jul. 27, 2006.
Office Action in co-pending U.S. Appl. No. 10/012,052, filed Nov. 17, 2006.
Office Action in co-pending U.S. Appl. No. 10/129,377, filed Oct. 10, 2006.
Office Action in co-pending U.S. Appl. No. 10/182,830, filed May 17, 2006.
Office Action in co-pending U.S. Appl. No. 10/203,254, filed Jun. 1, 2006.
Office Action in co-pending U.S. Appl. No. 10/312,083, filed Sep. 25, 2006.
Office Action in co-pending U.S. Appl. No. 10/459,636, filed Aug. 31, 2006.
Office Action in co-pending U.S. Appl. No. 10/699,780, filed Sep. 25, 2006.
Office Action in co-pending U.S. Appl. No. 10/746,612, filed Nov. 3, 2006.
Office Action in co-pending U.S. Appl. No. 10/990,475, filed May 1, 2006.
Office Action in co-pending U.S. Appl. No. 11/212,811, filed Aug. 24, 2006.
English language DERWENT Abstract for JP5-17710.
English language DERWENT Abstract for EP 1 382 322 A2.
English language DERWENT Abstract for FR 2 528 699.
English language DERWENT Abstract for JP 10/506643.
English language esp@cenet Abstract for FR 2 848 822 A1.
English language DERWENT Abstract for JP 10-158450.
English language DERWENT Abstract for JP 10-158451.
English language DERWENT Abstract for JP 2001-011340.
English language DERWENT Abstract for JP 7-258460.
English language DERWENT Abstract for JP 9-188830.
English language DERWENT Abstract for WO 96/38126.
English language esp@cenet abstract for EP 1 477 154 A1.
Irving R. Schmolka. PhD., "Gel Cosmetics," Cosmetics & Toiletries, vol. 99, pp. 69-76, Nov. 1984.
Office Action in co-pending U.S. Appl. No. 09/733,897, filed Jan. 18, 2007.
Office Action in co-pending U.S. Appl. No. 09/749,036, filed Jan. 17, 2007.
Office Action in co-pending U.S. Appl. No. 10/012,052, filed Jul. 5, 2007.
Office Action in co-pending U.S. Appl. No. 10/129,377, filed Jul. 13, 2007.

Office Action in co-pending U.S. Appl. No. 10/450,108, filed Mar. 21, 2007.
Office Action in co-pending U.S. Appl. No. 10/466,166, filed Jun. 25, 2007.
Office Action in co-pending U.S. Appl. No. 10/990,475, filed Jan. 23, 2007.
Office Action in co-pending U.S. Appl. No. 11/212,811, filed May 17, 2007.
Reexam Control No. 90/010,002; Title: Stable Cosmetic Emulsion With Polyamide Gelling Agent Filing Date: Jul. 18, 2007.
Continuation Application of Co-Pending U.S. Appl. No. 10/129,377; Title: Composition Structured With A Polymer Containing a Heteroatom and an Organogelator, filed Jul. 19, 2007.
Richard M. Sayre, "Physical Sunscreens," J. Soc. Cosmes. Chem., 41, 103-109 (Mar./Apr. 1990).
P. Terech, "Low Molecular Weight Organogelators," in Specialist Surfactants, ch. 8, pp. 208-268 (I.D. Robb, ed. 1997).

* cited by examiner

COSMETIC COMPOSITION COMPRISING A POLYMER BLEND

This is a continuation of application Ser. No. 10/012,029, filed Dec. 11, 2001, now U.S. Pat. No. 6,835,399, and claims benefit under 35 U.S.C. § 119(e) of U.S. Provisional Application No. 60/280,844, filed Apr. 3, 2001, both of which are incorporated herein by reference.

The present invention relates to a composition comprising, in a physiologically acceptable medium, a dispersion of film-forming polymer particles and a polymer containing a specific hetero atom, the composition being intended in particular for cosmetics. The invention also relates to a cosmetic make-up or care process for keratin materials. The make-up or care process and composition according to the invention are intended more particularly for the keratin materials of human beings, such as the skin (including the scalp), the nails, keratin fibers, especially substantially longilinear keratin fibers, such as the eyelashes, the eyebrows and the hair. The invention more especially relates to a mascara.

The composition according to the invention can be in the form of a coating composition for the eyelashes (in particular a mascara), an eyeliner, a product for the eyebrows, a product for the lips, a face powder, an eyeshadow, a foundation, a make-up product for the body, a concealer product, a nail varnish, a skincare product, including a product for scalp care, or a haircare product (hair mascara or spray).

The make-up composition may also be applied to make-up accessories (supports) such as false eyelashes, hairpieces, wigs or false nails or alternatively to pellets or patches adhering to the skin or the lips (such as beauty spots).

Compositions for coating the eyelashes, known as mascaras, generally comprise, in a known manner, at least one wax in the form of a wax-in-water emulsion, and at least one film-forming polymer to deposit a make-up film on the eyelashes and to coat them, for example as described in document WO-A-95/15741. Users expect these products to have good cosmetic properties, such as adhesion to the eyelashes, lengthening or curling of the eyelashes, or alternatively good staying power of the mascara over time, in particular good resistance to rubbing, for example with the fingers or fabrics (handkerchiefs or towels).

However, with these compositions, the make-up properties such as the coating, the lengthening or the curling of the eyelashes are obtained when a large amount of product is deposited on the eyelashes using an applicator, such as a mascara brush. When the composition does not adhere well to the eyelashes, the user must apply the brush impregnated with product onto the eyelashes several times, which requires a certain amount of time to be devoted to applying the make-up and obtaining the desired make-up results. However, this time may be perceived as far too long by users in a hurry. There is thus a need to have available mascaras that allow the expected make-up effect to be obtained quickly and easily.

The aim of the present invention is to provide a composition for making up keratin materials, especially keratin fibers such as the eyelashes, which applies easily to the keratin materials and leads quickly to a make-up effect with good cosmetic properties.

The inventors have found, surprisingly, that the use of a polymer containing a specific hetero atom in a composition comprising particles of a film-forming polymer dispersed in the medium of the composition makes it possible to improve the adhesion properties of the composition on keratin materials, especially on keratin fibers such as the eyelashes. The composition is easy to apply to the keratin materials and allows the composition to be deposited quickly in an amount that is sufficient to obtain a make-up effect with the expected cosmetic properties. In particular, a thick deposit of the make-up on the keratin materials is quickly obtained, which avoids the users having to spend too long applying the composition to the keratin materials.

Thus, for a mascara, a make-up which quickly thickens the keratin fibers, in particular the eyelashes, is obtained; instantaneous loading of the eyelashes is thus observed. The mascara also gives good lengthening to the made-up eyelashes.

More specifically, a subject of the invention is a composition comprising, in a physiologically acceptable medium, at least one first polymer with a weight-average molecular mass of less than 100 000, comprising a) a polymer skeleton containing hydrocarbon-based repeating units containing at least one hetero atom, and optionally b) at least one pendent fatty chain and/or at least one terminal fatty chain, which may be functionalized, containing from 6 to 120 carbon atoms and being linked to these hydrocarbon-based units, and a dispersion of particles of a second film-forming polymer that is insoluble in said medium.

A subject of the invention is also a cosmetic process for making up or caring for the keratin materials of human beings, comprising the application of a composition as defined above to the keratin materials. Preferably, the process applies to substantially longilinear keratin fibers such as the eyelashes, the hair and the eyebrows, and more especially to the eyelashes.

A subject of the invention is also the use of a composition as defined above to obtain a deposit which adheres to keratin materials and/or a quick make-up result on keratin materials.

Another subject of the invention is the use of a mascara comprising a composition as defined above to thicken quickly and/or to lengthen the eyelashes.

A subject of the invention is also the use, in a physiologically acceptable composition, of a combination of at least one first polymer with a weight-average molecular mass of less than 100 000 and better still less than 50 000, comprising a) a polymer skeleton containing hydrocarbon-based repeating units containing at least one hetero atom, and b) optionally at least one pendent fatty chain and/or at least one terminal fatty chain, which may be functionalized, containing from 6 to 120 carbon atoms and being linked to these hydrocarbon-based units, and at least one dispersion of particles [lacuna] a second film-forming polymer that is insoluble in said medium to obtain a deposit which adheres to keratin materials and/or a quick make-up result on keratin materials and/or to thicken quickly and/or lengthen the eyelashes.

The expression "physiologically acceptable medium" means a medium which is non-toxic and which can be applied to the skin, superficial body growths or the lips of human beings, such as a cosmetic medium.

For the purposes of the invention, the expression "functionalized chain" means an alkyl chain comprising one or more functional or reactive groups chosen in particular from amide, hydroxyl, ether, oxyalkylene, polyoxyalkylene and halogen groups, including fluoro or perfluoro groups, ester, siloxane and polysiloxane groups. In addition, the hydrogen atoms of one or more fatty chains may be substituted at least partially with fluorine atoms.

According to the invention, these chains may be linked directly to the polymer skeleton or via an ester function or a perfluoro group.

For the purposes of the invention, the term "polymer" means a compound containing at least 2 repeating units and preferably at least 3 repeating units.

For the purposes of the invention, the expression "hydrocarbon-based repeating units" means a unit containing from 2 to 80 carbon atoms and preferably from 2 to 60 carbon atoms, bearing hydrogen atoms and optionally oxygen atoms, which may be linear, branched or cyclic, and saturated or unsaturated. These units each also comprise one or more hetero atoms that are advantageously non-pendent but are in the polymer skeleton. These hetero atoms are chosen from nitrogen, sulfur and phosphorus atoms and combinations thereof, optionally combined with one or more oxygen atoms. The units preferably comprise at least one nitrogen atom, in particular a non-pendent nitrogen atom. These units also advantageously comprise a carbonyl group.

The units containing a hetero atom are, in particular, amide units forming a skeleton of the polyamide type, carbamate and/or urea units forming a polyurethane, polyurea and/or polyurea-urethane skeleton. These units are preferably amide units. The pendent chains are advantageously linked directly to at least one of the hetero atoms of the polymer skeleton.

Between the hydrocarbon-based units, the first polymer may comprise silicone units or oxyalkylene units.

In addition, the first polymer in the composition of the invention advantageously comprises from 40% to 98% of fatty chains relative to the total number of units containing a hetero atom and of fatty chains, and better still from 50% to 95%. The nature and proportion of the units containing a hetero atom depends on the nature of the fatty phase and is, in particular, similar to the polar nature of the fatty phase. Thus, the more the units containing a hetero atom are polar and in high proportion in the first polymer, which corresponds to the presence of several hetero atoms, the greater the affinity of the first polymer for polar oils. On the other hand, the less polar or even apolar the units containing a hetero atom or the lower their proportion, the greater the affinity of the first polymer for apolar oils.

The first polymer is advantageously a polyamide. Thus, a subject of the invention is also a composition containing, in a physiologically acceptable medium, at least one polyamide with a weight-average molecular mass of less than 100 000, comprising a) a polymer skeleton containing amide repeating units, and b) optionally at least one pendent fatty chain and/or at least one terminal chain, which may be functionalized, containing from 8 to 120 carbon atoms and being linked to these amide units, and at least one fiber.

The pendent fatty chains are preferably linked to at least one of the nitrogen atoms of the amide units of the first polymer.

In particular, the fatty chains of this polyamide represent from 40% to 98% of the total number of amide units and of fatty chains, and better still from 50% to 95%.

Advantageously, the first polymer, and in particular the polyamide, of the composition according to the invention has a weight-average molecular mass of less than 100 000 (especially ranging from 1 000 to 100 000), in particular less than 50 000 (especially ranging from 1 000 to 50 000) and more particularly ranging from 1 000 to 30 000, preferably from 2 000 to 20 000 and better still from 2 000 to 10 000.

As preferred first polymers which may be used in the invention, mention may be made of polyamides branched with pendent fatty chains and/or terminal fatty chains containing from 6 to 120 carbon atoms and better still from 8 to 120 and in particular from 12 to 68 carbon atoms, each terminal fatty chain being linked to the polyamide skeleton via at least one bonding group, in particular an ester. These polymers preferably comprise a fatty chain at each end of the polymer skeleton and in particular of the polyamide skeleton. Other bonding groups which may be mentioned are ether, amine, urea, urethane, thioester, thiourea and thiourethane groups.

These first polymers are preferably polymers resulting from a polycondensation between a dicarboxylic acid containing at least 32 carbon atoms (in particular containing from 32 to 44 carbon atoms) and a diamine containing at least 2 carbon atoms (in particular from 2 to 36 carbon atoms). The diacid is preferably a dimer of a fatty acid containing ethylenic unsaturation containing at least 16 carbon atoms, preferably from 16 to 24 carbon atoms, for instance oleic acid, linoleic acid or linolenic acid. The diamine is preferably ethylenediamine, hexylenediamine or hexamethylenediamine. For the polymers comprising one or 2 terminal carboxylic acid groups, it is advantageous to esterify them with a monoalcohol containing at least 4 carbon atoms, preferably from 10 to 36 carbon atoms, better still from 12 to 24 and even better from 16 to 24, for example 18 carbon atoms.

These polymers are more especially those disclosed in document U.S. Pat. No. 5,783,657 from the company Union Camp. Each of these polymers in particular satisfies formula (I) below:

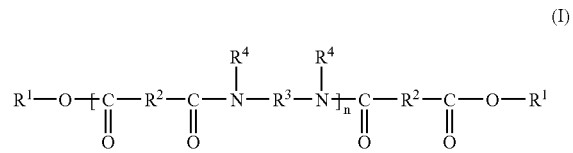

in which n denotes a number of amide units such that the number of ester groups represents from 10% to 50% of the total number of ester and amide groups; $R^1$ is, independently in each case, an alkyl or alkenyl group containing at least 4 carbon atoms and in particular from 4 to 24 carbon atoms; $R^2$ represents, independently in each case, a $C_4$ to $C_{42}$ hydrocarbon-based group, on condition that 50% of the groups $R^2$ represent a $C_{30}$ to $C_{42}$ hydrocarbon-based group; $R^3$ represents, independently in each case, an organic group containing at least 2 carbon atoms, hydrogen atoms and optionally one or more oxygen or nitrogen atoms; and $R^4$ represents, independently in each case, a hydrogen atom, a $C_1$ to $C_{10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R^4$ representing a hydrogen atom.

In the particular case of formula (I), the terminal fatty chains that are optionally functionalized for the purposes of the invention are terminal chains linked to the last hetero atom, in this case nitrogen, of the polyamide skeleton.

In particular, the ester groups of formula (I), which form part of the terminal and/or pendent fatty chains for the purposes of the invention, represent from 15% to 40% of the total number of ester and amide groups and better still from 20% to 35%. Furthermore, n is advantageously an integer ranging from 1 to 5 and better still greater than 2. Preferably, $R^1$ is a $C_{12}$ to $C_{22}$ and preferably $C_{16}$ to $C_{22}$ alkyl group. Advantageously, $R^2$ can be a $C_{10}$ to $C_{42}$ hydrocarbon-based (alkylene) group. Preferably, at least 50% and better still at least 75% of the groups $R^2$ are groups containing from 30 to 42 carbon atoms. The other groups $R^2$ are $C_4$ to $C_{18}$ and better still $C_4$ to $C_{12}$ hydrogen-containing groups. Preferably, $R^3$ represents a $C_2$ to $C_{36}$ hydrocarbon-based group or a polyoxyalkylene group and $R^4$ represents a hydrogen atom. Preferably, $R^3$ represents a $C_2$ to $C_{12}$ hydrocarbon-based group.

The hydrocarbon-based groups may be linear, cyclic or branched, and saturated or unsaturated groups. Moreover, the alkyl and alkylene groups may be linear or branched, and saturated or unsaturated groups.

In general, the polymers of formula (I) are in the form of mixtures of polymers, these mixtures also possibly containing a synthetic product corresponding to a compound of formula (I) in which n is 0, i.e. a diester.

As examples of first polymers according to the invention, mention may be made of the commercial products sold by the company Arizona Chemical under the names Uniclear® 80 and Uniclear® 100. They are sold, respectively, in the form of an 80% (in terms of active material) gel in a mineral oil and a 100% (in terms of active material) gel. They have a softening point of from 88 to 94° C. These commercial products are a mixture of copolymers of a $C_{36}$ diacid condensed with ethylenediamine, having a weight-average molecular mass of about 6 000. The terminal ester groups result from the esterification of the remaining acid endings with cetyl alcohol, stearyl alcohol or mixtures thereof (also known as cetylstearyl alcohol).

As first polymers which can be used in the invention, mention may also be made of polyamide resins resulting from the condensation of an aliphatic dicarboxylic acid and a diamine (including compounds containing more than 2 carbonyl groups and 2 amine groups), the carbonyl and amine groups of adjacent individual units being condensed via an amide bond. These polyamide resins are, in particular, those sold under the brand name Versamid® by the companies General Mills Inc. and Henkel Corp. (Versamid 930, 744 or 1655) or by the company Olin Mathieson Chemical Corp. under the brand name Onamid®, in particular Onamid S or C. These resins have a weight-average molecular mass ranging from 6 000 to 9 000. For further information regarding these polyamides, reference may be made to the documents U.S. Pat. No. 3,645,705 and U.S. Pat. No. 3,148,125. More especially, Versamid® 930 or 744 is used.

The polyamides sold by the company Arizona Chemical under the references Uni-Rez® (2658, 2931, 2970, 2621, 2613, 2624, 2665, 1554, 2623 and 2662) and the product sold under the reference Macromelt 6212 by the company Henkel may also be used. For further information regarding these polyamides, reference may be made to document U.S. Pat. No. 5,500,209.

It is also possible to use polyamide resins obtained from plants, such as those disclosed in patents U.S. Pat. No. 5,783,657 and U.S. Pat. No. 5,998,570.

The first polymer present in the composition according to the invention advantageously has a softening point of greater than 65° C., which may be up to 190° C. It preferably has a softening point ranging from 70° C. to 130° C. and better still from 80° C. to 105° C. The first polymer is in particular a non-waxy polymer.

The first polymer according to the invention preferably corresponds to the formula (I) mentioned above. On account of its fatty chain(s), this first polymer is readily soluble in oils and thus leads to compositions that are macroscopically homogeneous even with a high content (at least 25%) of polymer, unlike polymers not containing a fatty chain.

The first polymer may be present in the composition according to the invention in a content ranging from 0.01% to 10% by weight, relative to the total weight of the composition, preferably ranging from 0.05% to 5% by weight and better still ranging from 0.1% to 3% by weight.

The composition according to the invention may comprise a fatty phase which can comprise fatty substances chosen from oils, organic solvents, waxes and pasty fatty substances, and mixtures thereof. The fatty phase can form a continuous phase of the composition. In particular, the composition according to the invention may be anhydrous.

The fatty phase may especially consist of any oil which is physiologically acceptable and in particular cosmetically acceptable, chosen especially from oils of mineral, animal, plant or synthetic origin, carbon-based oils, hydrocarbon-based oils, fluoro oils and/or silicone oils, alone or as a mixture, provided that they form a homogeneous and stable mixture and provided that they are compatible with the intended use.

The total fatty phase of the composition, which may be a liquid fatty phase, can represent from 2% to 98% by weight, relative to the total weight of the composition, and preferably from 5% to 85% by weight.

The fatty phase of the composition can advantageously comprise at least one volatile oil or organic solvent and/or at least one non-volatile oil.

For the purposes of the invention, the expression "volatile oil or organic solvent" means any non-aqueous medium which can evaporate on contact with the skin in less than one hour at room temperature and atmospheric pressure. The volatile organic solvent(s) and the volatile oils of the invention are volatile cosmetic organic solvents and oils, that are liquid at room temperature, having a non-zero vapour pressure at room temperature and atmospheric pressure, ranging in particular from $10^{-2}$ to 300 mmHg (0.13 Pa to 40 000 Pa) and preferably greater than 0.3 mmHg (30 Pa). The expression "non-volatile oil" means an oil which remains on the skin at room temperature and atmospheric pressure for at least several hours and which in particular has a vapour pressure of less than $10^{-2}$ mmHg (1.33 Pa).

These oils may be hydrocarbon-based oils, silicone oils or fluoro oils, or mixtures thereof.

The expression "hydrocarbon-based oil" means an oil mainly containing hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, and especially $C_8$-$C_{16}$ branched alkanes, for instance $C_8$-$C_{16}$ isoalkanes of petroleum origin (also known as isoparaffins), for instance isododecane (also known as 2,2,4,4,6-pentamethylheptane), isodecane and isohexadecane, and, for example, the oils sold under the trade names Isopars or Permetyls, $C_8$-$C_{16}$ branched esters, isohexyl neopentanoate, and mixtures thereof. Other volatile hydrocarbon-based oils, for instance petroleum distillates, especially those sold under the name Shell Solt by the company Shell, may also be used. The volatile solvent is preferably chosen from hydrocarbon-based volatile oils containing from 8 to 16 carbon atoms, and mixtures thereof.

Volatile oils which may also be used are volatile silicones such as, for example, linear or cyclic volatile silicone oils, especially those with a viscosity $\leqq 8$ centistokes ($8\times10^{-6}$ $m^2$/s) and especially containing from 2 to 7 silicon atoms, these silicones optionally comprising alkyl or alkoxy groups containing from 1 to 10 carbon atoms. As volatile silicone oils which may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro solvents such as nonafluoromethoxybutane or perfluoromethylcyclopentane may also be used.

The volatile oil may be present in the composition according to the invention in a content ranging from 0% to 98% by weight (in particular from 0.1% to 98%), relative to the total weight of the composition, preferably from 0% to 65% by weight (in particular from 1% to 65%).

The composition can also comprise at least one non-volatile oil chosen in particular from non-volatile hydrocarbon-based and/or silicone and/or fluoro oils.

Non-volatile hydrocarbon-based oils which may be mentioned in particular are:

hydrocarbon-based plant oils such as triglycerides consisting of fatty acid esters and of glycerol in which the fatty acids may have varied chain lengths from $C_4$ to $C_{24}$, these chains possibly being linear or branched, and saturated or unsaturated; these oils are, in particular, wheat germ oil, sunflower oil, grape seed oil, sesame oil, corn oil, apricot oil, castor oil, karite butter, avocado oil, olive oil, soybean oil, sweet almond oil, palm oil, rape seed oil, cotton oil, hazelnut oil, macadamia oil, jojoba oil, alfalfa oil, poppy oil, pumpkin oil, marrow oil, blackcurrant seed oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810, 812 and 818 by Dynamit Nobel;

synthetic ethers containing from 10 to 40 carbon atoms;

linear or branched hydrocarbons of mineral or synthetic origin, such as petroleum jelly, polydecenes, hydrogenated polyisobutene such as parleam, and squalane, and mixtures thereof;

synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_5+R_6 \geq 10$, such as, for example, purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid;

and mixtures thereof.

The non-volatile silicone oils which may be used in the composition according to the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenylsilicones, for instance phenyltrimethicones, phenyldimethicones, phenyltrimethylsiloxydiphenylsiloxanes, diphenyldimethicones, diphenylmethyldiphenyltrisiloxanes and 2-phenylethyl trimethylsiloxysilicates.

The fluoro oils which may be used in the invention are, in particular, fluorosilicone oils, fluoropolyethers or fluorosilicones, as described in document EP-A-847 752.

The non-volatile oils may be present in the composition according to the invention in a content ranging from 0% to 80% (in particular from 0.1% to 80%) by weight, preferably from 0% to 50% by weight (in particular 0.1% to 50% by weight), relative to the total weight of the composition, and better still from 0% to 20% by weight (in particular 0.1% to 20%).

The composition according to the invention can also comprise a wax. For the purposes of the present invention, the term "wax" means a lipophilic fatty compound that is solid at room temperature (25° C.) and atmospheric pressure (760 mmHg, i.e. $10^5$ Pa), which undergoes a reversible solid/liquid change of state and which has a melting point of greater than 30° C. and better still greater than 55° C., which may be up to 200° C., in particular up to 120° C.

By taking the wax to its melting point, it is possible to make it miscible with oils and to form a microscopically homogeneous mixture, but on returning the temperature of the mixture to room temperature, recrystallization of the wax in the mixture of oils is obtained.

According to the invention, the melting point values correspond to the melting peak measured using a differential scanning calorimeter (DSC), for example the calorimeter sold under the name DSC 30 by the company Mettler, with a temperature increase of 5 or 10° C. per minute.

For the purposes of the invention, the waxes are those generally used in cosmetics and dermatology. Mention may be made in particular of beeswax, lanolin wax, Chinese insect waxes, rice wax, carnauba wax, candelilla wax, ouricury wax, cork fiber wax, sugar cane wax, Japan wax, sumach wax, montan wax, microcrystalline waxes, paraffin waxes, ozokerites, ceresin wax, lignite wax, polyethylene waxes and the waxes obtained by Fisher-Tropsch synthesis, and fatty acid esters of glycerides that are solid at 40° C. and better still at more than 55° C. Mention may also be made of the waxes obtained by catalytic hydrogenation of animal or plant oils containing linear or branched $C_8$-$C_{32}$ fatty chains. Among these, mention may be made in particular of hydrogenated jojoba oil, hydrogenated sunflower oil, hydrogenated castor oil, hydrogenated coconut oil and hydrogenated lanolin oil.

Mention may also be made of silicone waxes or fluoro waxes.

The waxes present in the composition may be dispersed in the form of particles in an aqueous phase as defined below. These particles may have an average size ranging from 50 nm to 10 µm and preferably from 50 nm to 3.5 µm.

In particular, the wax may be present in the form of a wax-in-water emulsion, the waxes possibly being in the form of particles with an average size ranging from 1 µm to 10 µm and preferably from 1 µm to 3.5 µm.

In another embodiment of the composition according to the invention, the wax may be present in the form of a wax microdispersion, the wax being in the form of particles with an average size of less than 1 µm and in particular ranging from 50 nm to 500 nm. Wax microdispersions are disclosed in documents EP-A-557 196 and EP-A-1 048 282.

The wax may also be present in a liquid fatty phase as a mixture with oils such as defined above.

The wax may also have a hardness ranging from 0.05 MPa to 15 MPa and preferably ranging from 6 MPa to 15 MPa. The hardness is determined by measuring the compressive strength, measured at 20° C. using a texturometer sold under the name TA-XT2i by the company Rheo, equipped with a stainless steel cylinder 2 mm in diameter travelling at a measuring speed of 0.1 mm/s, and penetrating into the wax to a penetration depth of 0.3 mm. To carry out the hardness measurement, the wax is melted at a temperature equal to the melting point of the wax +20° C. The molten wax is cast in a container 30 mm in diameter and 20 mm deep. The wax is recrystallized at room temperature (25° C.) over 24 hours and is then stored for at least one hour at 20° C. before carrying out the hardness measurement. The value of the hardness is the compressive strength measured divided by the area of the texturometer cylinder in contact with the wax.

The wax may be present in the composition according to the invention in a content ranging from 0.1% to 50% by weight, relative to the total weight of the composition, preferably from 0.5% to 30% by weight and better still from 1% to 20% by weight.

The composition according to the invention may contain at least one fatty compound that is pasty at room temperature. For the purposes of the invention, the expression "pasty fatty substance" means fatty substances with a melting point ranging from 20 to 55° C., preferably 25 to 45° C., and/or a viscosity at 40° C. ranging from 0.1 to 40 Pa.s (1 to 400 poises), preferably 0.5 to 25 Pa.s, measured using a Contraves TV or Rhéomat 80 viscometer, equipped with a spindle rotating at 60 Hz. A person skilled in the art can select the spindle for measuring the viscosity from the spindles MS-r3 and MS-r4, on the basis of his general knowledge, so as to be able to carry out the measurement of the pasty compound tested.

These fatty substances are preferably hydrocarbon-based compounds, optionally of polymeric type; they can also be chosen from silicone compounds and/or fluoro compounds; they may also be in the form of a mixture of hydrocarbon-based compounds and/or silicone compounds and/or fluoro compounds. In the case of a mixture of different pasty fatty substances, the hydrocarbon-based pasty compounds (containing mainly hydrogen and carbon atoms and optionally ester groups) are preferably used in major proportion.

Among the pasty compounds which may be used in the composition according to the invention, mention may be made of lanolins and lanolin derivatives such as acetylated lanolins or oxypropylenated lanolins or isopropyl lanolate, having a viscosity of from 18 to 21 Pa.s, preferably 19 to 20.5 Pa.s, and/or a melting point of from 30 to 55° C., and mixtures thereof. It is also possible to use esters of fatty acids or of fatty alcohols, in particular those containing from 20 to 65 carbon atoms (melting point of about from 20 to 35° C. and/or viscosity at 40° C. ranging from 0.1 to 40 Pa.s), such as triisostearyl or cetyl citrate; arachidyl propionate; polyvinyl laurate; cholesterol esters, such as triglycerides of plant origin, such as hydrogenated plant oils, viscous polyesters such as poly(12-hydroxystearic acid), and mixtures thereof. Triglycerides of plant origin which may be used are hydrogenated castor oil derivatives, such as "Thixinr" from Rhéox.

Mention may also be made of pasty silicone fatty substances such as polydimethylsiloxanes (PDMSs) containing pendent chains of the alkyl or alkoxy type containing from 8 to 24 carbon atoms, and having a melting point of 20-55° C., such as stearyldimethicones, in particular those sold by Dow Corning under the trade names DC2503 and DC25514, and mixtures thereof.

The pasty fatty substance may be present in the composition according to the invention in a proportion of from 0% to 60% (in particular 0.01% to 60%) by weight, relative to the total weight of the composition, preferably in a proportion of from 0.5% to 45% by weight, and better still ranging from 2% to 30% by weight, in the composition.

The composition according to the invention may also comprise an aqueous medium, constituting an aqueous phase, which may be the continuous phase of the composition.

The aqueous phase may consist essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, $C_3$-$C_4$ ketones and $C_2$-$C_4$ aldehydes.

The aqueous phase (water and optionally the water-miscible organic solvent) may be present in a content ranging from 1% to 95% by weight, relative to the total weight of the composition, preferably from 3% to 80% by weight and better still from 5% to 60% by weight.

The composition according to the invention can contain emulsifying surfactants, present in particular in a proportion ranging from 2% to 30% by weight relative to the total weight of the composition, and better still from 5% to 15%. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants preferably used in the composition according to the invention are chosen from:
  nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of $C_1$-$C_6$ alkyl glucose, and mixtures thereof;
  anionic surfactants: $C_{16}$-$C_{30}$ fatty acids neutralized with amines, aqueous ammonia or alkaline salts, and mixtures thereof.

Surfactants which make it possible to obtain an oil-in-water or wax-in-water emulsion are preferably used.

The composition according to the invention comprises at least one second film-forming polymer, different from the first polymer described above, in the form of solid particles dispersed in the physiologically acceptable medium. These particles may be dispersed in an aqueous phase or in a liquid fatty phase. The composition can comprise a mixture of these polymers. The second film-forming polymer is insoluble in the medium of the composition, that is to say that it remains in the form of particles in the mixture of the ingredients of the composition forming the physiologically acceptable medium. Thus, the expression "polymer that is insoluble in the physiologically acceptable medium" should be understood as meaning a polymer whose solubility in this medium is less than 1% by weight.

The second film-forming polymer may be present in the composition according to the invention in a solids content ranging from 0.1% to 60% by weight relative to the total weight of the composition, preferably from 0.5% to 40% by weight and better still from 1% to 30% by weight.

In the present application, the expression "film-forming polymer" means a polymer which is capable, by itself or in the presence of an auxiliary film-forming agent, of forming a continuous and adherent film on a support, in particular on keratin materials.

A film-forming polymer capable of forming a hydrophobic film, i.e. a polymer whose film has a water-solubility at 25° C. of less than 1% by weight, is preferably used.

Among the film-forming polymers which may be used in the composition of the present invention, mention may be made of synthetic polymers, of radical-mediated type or of polycondensate type, and polymers of natural origin, and mixtures thereof.

The expression "radical-mediated film-forming polymer" means a polymer obtained by polymerization of monomers containing unsaturation, in particular ethylenic unsaturation, each monomer being capable of homopolymerizing (unlike polycondensates).

The film-forming polymers of radical-mediated type may be, in particular, vinyl polymers or copolymers, in particular acrylic polymers.

The vinyl film-forming polymers can result from the polymerization of monomers containing ethylenic unsaturation and containing at least one acidic group and/or esters of these acidic monomers and/or amides of these acidic monomers.

Monomers bearing an acidic group which may be used are α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acidic monomers are advantageously chosen from (meth)acrylic acid esters (also known as (meth)acrylates), especially (meth)acrylates of an alkyl, in particular of a $C_1$-$C_{30}$ and preferably $C_1$-$C_{20}$ alkyl, (meth)acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates which may be mentioned are methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates which may be mentioned are hydroxyethyl acrylate, 2-hydroxypropyl acrylate, hydroxyethyl methacrylate and 2-hydroxypropyl methacrylate.

Among the aryl (meth)acrylates which may be mentioned are benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted with fluorine atoms.

As amides of the acidic monomers, mention may be made, for example, of (meth)acrylamides, and especially N-alkyl(meth)acrylamides, in particular of a $C_2$-$C_{12}$ alkyl. Among the N-alkyl(meth)acrylamides which may be mentioned are N-ethylacrylamide, N-t-butylacrylamide, N-t-octylacrylamide and N-undecylacrylamide.

The vinyl film-forming polymers can also result from the homopolymerization or copolymerization of monomers chosen from vinyl esters and styrene monomers. In particular, these monomers may be polymerized with acidic monomers and/or esters thereof and/or amides thereof, such as those mentioned above.

Examples of vinyl esters which may be mentioned are vinyl acetate, vinyl neodecanoate, vinyl pivalate, vinyl benzoate and vinyl t-butylbenzoate.

Styrene monomers which may be mentioned are styrene and α-methylstyrene.

It is possible to use any monomer known to those skilled in the art which falls within the categories of acrylic and vinyl monomers (including monomers modified with a silicone chain).

Among the film-forming polycondensates which may be mentioned are polyurethanes, polyesters, polyesteramides, polyamides, epoxy ester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, in particular diols.

The dicarboxylic acid may be aliphatic, alicyclic or aromatic. Examples of such acids which may be mentioned are: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. Among these monomers, the ones preferably chosen are phthalic acid, isophthalic acid and terephthalic acid.

The diol may be chosen from aliphatic, alicyclic and aromatic diols. The diol preferably used is one chosen from: ethylene glycol, diethylene glycol, triethylene glycol, 1,3-propanediol, cyclohexanedimethanol, 4-butanediol. Other polyols which may be used are glycerol, pentaerythritol, sorbitol and trimethylolpropane.

The polyesteramides may be obtained in a manner analogous to that of the polyesters, by polycondensation of diacids with diamines or amino alcohols. Diamines which may be used are ethylenediamine, hexamethylenediamine and meta- or para-phenylenediamine. An amino alcohol which may be used is monoethanolamine.

The polyester may also comprise at least one monomer bearing at least one group —$SO_3M$, with M representing a hydrogen atom, an ammonium ion $NH_4^+$ or a metal ion such as, for example, an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may be used in particular.

The aromatic nucleus of the difunctional aromatic monomer also bearing a group —$SO_3M$ as described above may be chosen, for example, from benzene, naphthalene, anthracene, biphenyl, oxybiphenyl, sulfonylbiphenyl and methylenebiphenyl nuclei. As examples of difunctional aromatic monomers also bearing a group —$SO_3M$, mention may be made of: sulfoisophthalic acid, sulfoterephthalic acid, sulfophthalic acid, 4-sulfonaphthalene-2,7-dicarboxylic acid.

The copolymers preferably used are those based on isophthalate/sulfoisophthalate, and more particularly copolymers obtained by condensation of diethylene glycol, cyclohexanedimethanol, isophthalic acid and sulfoisophthalic acid.

Such polymers are sold, for example, under the brand name Eastman AQ® by the company Eastman Chemical Products.

The polymers of natural origin, optionally modified, may be chosen from shellac resin, sandarac gum, dammar resins, elemi gums, copal resins and cellulose polymers, and mixtures thereof.

According to a first embodiment of the composition according to the invention, the second film-forming polymer may be present in the form of particles in dispersion in an aqueous phase, which is generally known as a latex or pseudolatex. The techniques for preparing these dispersions are well known to those skilled in the art.

Aqueous dispersions of film-forming polymers which may be used are the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company Goodrich, Impranil 85® by the company Bayer and Aquamere H-1511® by the company Hydromer.

Aqueous dispersions of film-forming polymers which may also be used are the polymer dispersions resulting from the radical-mediated polymerization of one or more radical-mediated monomers within and/or partially at the surface of pre-existing particles of at least one polymer chosen from the group consisting of polyurethanes, polyureas, polyesters, polyesteramides and/or alkyds. These polymers are generally referred to as hybrid polymers.

Furthermore, the aqueous phase of the composition may comprise an additional water-soluble polymer present in the aqueous medium of the composition in dissolved form. Examples of water-soluble film-forming polymers which may be mentioned are:

proteins, for instance proteins of plant origin such as wheat proteins and soybean proteins; proteins of animal origin such as keratins, for example keratin hydrolysates and sulfonic keratins;

anionic, cationic, amphoteric or nonionic chitin or chitosan polymers;

polymers of celluloses such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

polymers of natural origin, which are optionally modified, such as:

gum arabics, guar gum, xanthan derivatives, karaya gum; alginates and carrageenans;

glycoaminoglycans, hyaluronic acid and derivatives thereof;

shellac resin, sandarac gum, dammar resins, elemi gums and copal resins;

deoxyribonucleic acid;

mucopolysaccharides such as hyaluronic acid and chondroitin sulfate, and mixtures thereof.

According to another embodiment of the composition according to the invention, the second film-forming polymer may be present in the form of surface-stabilized particles dispersed in a liquid fatty phase comprising organic solvents or oils such as those described above. For the purposes of the invention, the expression "liquid fatty phase" means a fatty phase which is liquid at room temperature (25° C.) and atmospheric pressure (760 mmHg, i.e. $10^5$ Pa), composed of one or more fatty substances that are liquid at room temperature, also known as oils, which are generally mutually compatible.

The liquid fatty phase preferably comprises a volatile oil, optionally mixed with a non-volatile oil, the oils possibly being chosen from those mentioned above.

The dispersion of surface-stabilized polymer particles may be manufactured as disclosed in document EP-A-749 747. It may be obtained by dispersion polymerization, that is to say by precipitating the polymer during formation, with protection of the formed particles using a stabilizer.

The choice of the liquid fatty phase is made by a person skilled in the art as a function of the nature of the monomers constituting the polymer and/or of the nature of the stabilizer, as indicated below.

The polymer particles are surface-stabilized by means of a stabilizer which may be a block polymer, a grafted polymer and/or a random polymer, alone or as a mixture.

Dispersions of film-forming polymer in the liquid fatty phase, in the presence of stabilizers, are disclosed in particular in documents EP-A-0 749 746, EP-A-0 923 928 and EP-A-0 930 060, the content of which is incorporated in the present patent application by reference.

Among the grafted polymers that may be mentioned are silicone polymers grafted with a hydrocarbon-based chain; hydrocarbon-based polymers grafted with a silicone chain.

Grafted copolymers having, for example, an insoluble skeleton of polyacrylic type with soluble grafts of poly(12-hydroxystearic acid) type are also suitable.

Grafted-block or block copolymers comprising at least one block of polyorganosiloxane type and at least one block of a free-radical polymer may also be used, for instance grafted copolymers of acrylic/silicone type which may be used especially when the non-aqueous medium is silicone-based.

The stabilizer may also be chosen from grafted-block or block copolymers comprising at least one block of polyorganosiloxane type and at least one block of a polyether. The polyorganosiloxane block may especially be a polydimethylsiloxane or a poly($C_2$-$C_{18}$)alkylmethylsiloxane; the polyether block may be a $C_2$-$C_{18}$ polyalkylene, in particular polyoxyethylene and/or polyoxypropylene. In particular, dimethicone copolyols or ($C_2$-$C_{18}$)alkylmethicone copolyols may be used. It is possible, for example, to use the dimethicone copolyol sold under the name "Dow Corning 3225C" by the company Dow Corning, or the lauryl methicone copolyol sold under the name "Dow Corning Q2-5200" by the company Dow Corning.

As grafted-block or block copolymers, use may be made of copolymers comprising at least one block resulting from the polymerization of at least one ethylenic monomer, containing one or more optionally conjugated ethylenic bonds, such as ethylene, butadiene or isoprene, and at least one block of a styrene polymer. When the ethylenic monomer comprises several optionally conjugated ethylenic bonds, the residual ethylenic unsaturations after the polymerization are generally hydrogenated. Thus, in a known manner, the polymerization of isoprene leads, after hydrogenation, to the formation of ethylene-propylene block, and the polymerization of butadiene leads, after hydrogenation, to the formation of ethylene-butylene block. Among these block copolymers, mention may be made of copolymers of "diblock" or "triblock" type, of the type such as polystyrene/polyisoprene, polystyrene/polybutadiene such as those sold under the name "Luvitol HSB" by BASF, of the polystyrene/copoly(ethylene-propylene) type such as those sold under the name "Kraton" by Shell Chemical Co., or alternatively of the polystyrene/copoly(ethylene-butylene) type.

As grafted-block or block copolymers comprising at least one block resulting from the polymerization of at least one ethylenic monomer, such as ethylene or isobutylene, and of at least one block of an acrylic polymer such as methyl methacrylate, mention may be made of the poly(methyl methacrylate)/polyisobutylene diblock or triblock copolymers or the grafted copolymers containing a poly(methyl methacrylate) skeleton and polyisobutylene grafts.

As grafted-block or block copolymers comprising at least one block resulting from the polymerization of at least one ethylenic monomer and of at least one block of a polyether such as a $C_2$-$C_{18}$ polyoxyalkylene, in particular polyoxyethylene and/or polyoxypropylene, mention may be made of polyoxyethylene/polybutadiene or polyoxyethylene/polyisobutylene diblock or triblock copolymers.

Use may also be made of copolymers of $C_1$-$C_4$ alkyl (meth)acrylates, and of $C_8$-$C_{30}$ alkyl (meth)acrylates. Mention may be made in particular of the stearyl methacrylate/methyl methacrylate copolymer.

In this case, it is then preferred to use as stabilizer either a grafted polymer or a block polymer, so as to have better interfacial activity. Specifically, the blocks or grafts that are insoluble in the synthesis solvent provide a more voluminous coverage at the surface of the particles.

When the liquid fatty phase comprises at least one silicone oil, the stabilizer is preferably chosen from the group consisting of grafted-block or block copolymers comprising at least one block of polyorganosiloxane type and at least one block of a free-radical polymer or of a polyether or of a polyester, for instance polyoxy($C_2$-$C_{18}$)alkylene blocks and especially polyoxypropylene and/or oxyethylene blocks.

When the liquid fatty phase does not comprise a silicone oil, the stabilizer is preferably chosen from the group consisting of:
(a) grafted-block or block copolymers comprising at least one block of polyorganosiloxane type and at least one block of a free-radical polymer or of a polyether or of a polyester,
(b) copolymers of $C_1$-$C_4$ alkyl acrylates or methacrylates and of $C_8$-$C_{30}$ alkyl acrylates or methacrylates,
(c) grafted-block or block copolymers comprising at least one block resulting from the polymerization of at least one ethylenic monomer containing conjugated ethylenic bonds, and at least one block of a vinyl or acrylic polymer or of a polyether or of a polyester, or blends thereof.

Diblock polymers are preferably used as stabilizer.

The size of the particles of the second film-forming polymer dispersed either in the aqueous phase or in the liquid fatty phase can range from 5 nm to 600 nm and preferably from 20 nm to 300 nm.

The composition according to the invention may comprise an auxiliary film-forming agent for promoting the formation of a film with the second film-forming polymer. Such a film-forming agent may be chosen from any compound known to those skilled in the art as being capable of fulfilling the desired function, and may be chosen in particular from plasticizers and coalescers.

In addition, the liquid fatty phase may also contain a third additional film-forming polymer dissolved in the liquid fatty phase, also known as a liposoluble polymer.

Liposoluble polymers that may especially be mentioned include copolymers resulting from the copolymerization of at least one vinyl ester and of at least one other monomer which may be an olefin, an alkyl vinyl ether or an allylic or methallylic ester, as described in patent application FR-A-2 232 303, the content of which is incorporated into the present patent application by reference.

As liposoluble film-forming polymers which may be used in the invention, mention may also be made of polyalkylenes and in particular copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) and in particular copolymers of vinylpyrrolidone and of $C_2$ to $C_{40}$ and better still $C_3$ to $C_{20}$ alkene. As examples of VP copolymers which may be used in the invention, mention may be made of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The liposoluble film-forming polymer may be present in the composition in a content ranging from 0.1% to 15% by weight and better still from 2% to 10% by weight relative to the total weight of the composition.

The composition according to the invention may also comprise a dyestuff, for instance pulverulent dyestuffs, liposoluble dyes and water-soluble dyes. This dyestuff may be present in a content ranging from 0.01% to 30% by weight, relative to the total weight of the composition.

The pulverulent dyestuffs may be chosen from pigments and nacres.

The pigments may be white or colored, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D & C type, and lakes based on cochineal carmine or on barium, strontium, calcium or aluminum.

The nacres may be chosen from white nacreous pigments such as mica coated with titanium or with bismuth oxychloride, colored nacreous pigments such as titanium mica with iron oxides, titanium mica with, in particular, ferric blue or chromium oxide, titanium mica with an organic pigment of the abovementioned type, and nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice and methylene blue.

The composition of the invention may also comprise any additive usually used in cosmetics, such as antioxidants, fillers, preserving agents, fragrances, neutralizing agents, thickeners, cosmetic or dermatological active agents such as, for example, emollients, moisturizers, vitamins and sunscreens, and mixtures thereof. These additives may be present in the composition in a content ranging from 0% to 20% (in particular from 0.01% to 20%) relative to the total weight of the composition and better still from 0.01% to 10% (if present).

Needless to say, a person skilled in the art will take care to select the optional additional additives and/or the amount thereof such that the advantageous properties of the composition according to the invention are not, or are not substantially, adversely affected by the addition envisaged.

The composition according to the invention may be manufactured by the known processes generally used in cosmetics or dermatology.

The invention is illustrated in greater detail in the examples which follow.

EXAMPLE 1

A mascara having the composition below was prepared:

| | |
|---|---|
| Carnauba wax | 2.6 g |
| Beeswax | 3.3 g |
| Paraffin wax | 10.4 g |
| Hydrogenated jojoba oil | 0.2 g |
| Hydrogenated palm oil | 0.2 g |
| Polyamide resin with ester end groups, sold under the name "Uniclear ® 100" by the company Arizona Chemical | 1 g |
| 2-Amino-2-methyl-1,3-propanediol | 0.8 g |
| Triethanolamine | 2.4 g |
| Stearic acid | 6.6 g |
| Hydroxyethylcellulose | 0.8 g |
| Gum arabic | 0.6 g |
| Ethyl acrylate/methyl methacrylate copolymer (80/20) as an aqueous dispersion containing 50% AM (Daitosol 5000 AD from Saito) | 7 g AM |
| Black iron oxide | 5 g |
| Preserving agents | qs |
| Water | qs 100 g |

This mascara is easy to apply and adheres well to the eyelashes during and after application; the eyelashes are made up quickly. It also gives instantaneous loading of the eyelashes.

A mascara composition having the composition below was prepared:

| | |
|---|---|
| Carnauba wax | 4.6 g |
| Rice bran wax | 2.1 g |
| Paraffin | 2.2 g |
| Beeswax | 8.2 g |
| Polyamide resin with ester end groups, sold under the name "Uniclear ® 100" by the company Arizona Chemical | 1 g |
| Talc | 1 g |
| Bentonite | 5 g |
| Vinyl acetate/allyl stearate copolymer (65/35) (Mexomère PQ from Chimex) | 6.5 g |
| Polyvinyl laurate (Mexomère PP from Chimex) | 0.7 g |
| Sulphopolyester (AQ 55S from Eastman Chemical) | 0.12 g |
| Isododecane | 53.9 g |
| Propylene carbonate | 1.6 g |
| Pigments | 4.9 g |
| Preserving agents | qs |
| Water | qs 100 g |

This is mascara adheres well to the eyelashes during and after application. It gives the eyelashes good instantaneous loading.

EXAMPLE 3 a) Dispersion of polymer in isododecane used:

A dispersion of non-crosslinked copolymer of methyl acrylate and of acrylic acid in a 95/5 ratio, in isododecane, was prepared according to the method of Example 7 of document EP-A-749 747. A dispersion is thus obtained of particles of poly(methyl acrylate/acrylic acid) surface-stabilized in isododecane with a polystyrene/copoly(ethylene-propylene) diblock block copolymer sold under the name Kraton G1701 (Shell), with a solids content of 24.2% by weight, a mean particle size of 180 nm and a Tg of 20° C. This copolymer can form a film at room temperature.

b) A mascara having the composition below was prepared:

| | |
|---|---|
| Carnauba wax | 4.7 g |
| Rice bran wax | 2.1 g |
| Paraffin | 2.2 g |
| Beeswax | 8.2 g |
| Polyamide resin with ester end groups, sold under the name "Uniclear ® 100" by the company Arizona Chemical | 0.5 g |
| Dispersion of polymer in isododecane according to a) | 10 g |
| Talc | 1 g |
| Bentonite | 5 g |
| Vinyl acetate/allyl stearate copolymer (65/35) (Mexomère PQ from Chimex) | 6.5 g |
| Polyvinyl laurate (Mexomère PP from Chimex) | 0.7 g |
| Propylene carbonate | 1.6 g |
| Pigments | 4.9 g |
| Preserving agents | qs |
| Isododecane | qs 100 g |

This mascara adheres well to the eyelashes during and after application. It gives the eyelashes good instantaneous loading.

The invention claimed is:

1. A cosmetic composition comprising, in a physiologically acceptable medium, at least one first polymer of formula (I):

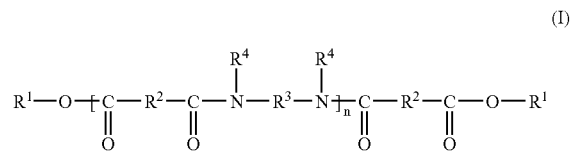

wherein:

n is an integer which represents the number of amide units such that the number of ester groups present in said at least one first polymer ranges from 10% to 50% of the total number of all said ester groups and all said amide groups comprised in said at least one first polymer;

$R^1$, which are identical or different, are each chosen from alkyl groups comprising at least four carbon atoms and alkenyl groups comprising at least four carbon atoms;

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising at least two carbon atoms, hydrogen atoms, and optionally at least one entity chosen from oxygen and nitrogen atoms; and R⁴, which are identical or different, are each chosen from hydrogen, $C_1$ to $C_{10}$ alkyl groups, and a direct bond to R³ or another R⁴, such that the nitrogen atom to which R³ and R⁴ are both attached forms part of a heterocyclic structure defined by R⁴-N-R³, with the proviso that at least 50% of all R⁴ are chosen from hydrogen;

and a dispersion of particles of at least one second polymer that is film-forming and insoluble in said medium.

2. The composition of claim 1, wherein the at least one first polymer has a weight-average molecular mass ranging from 1,000 to 100,000.

3. The composition of claim 2, wherein the at least one first polymer has a weight-average molecular mass ranging from 1,000 to 50,000.

4. The composition of claim 3, wherein the at least one first polymer has a weight-average molecular mass ranging from 1,000 to 30,000.

5. The composition of claim 1, wherein the at least one first polymer is chosen from ethylenediamine/stearyl dimer tallate copolymer and ethylenediamine/stearyl dimer dilinoleate copolymer.

6. The composition of claim 1, wherein the at least one first polymer is present in the composition in an amount ranging from 0.01% to 10% by weight, relative to the total weight of the composition.

7. The composition of claim 6, wherein the at least one first polymer is present in the composition in an amount ranging from 0.05% to 5% by weight, relative to the total weight of the composition.

8. The composition of claim 7, wherein the at least one first polymer is present in the composition in an amount ranging from 0.1% to 3% by weight, relative to the total weight of the composition.

9. The composition of claim 1, wherein the at least one second polymer is chosen from radical-mediated polymers, polycondensates, polymers of natural origin, and mixtures thereof.

10. The composition of claim 1, wherein the at least one second polymer is chosen from vinyl polymers, polyurethanes, polyesters, cellulose polymers, and mixtures thereof.

11. The composition of claim 1, further comprising an aqueous phase.

12. The composition of claim 11, wherein the aqueous phase comprises at least one water-soluble film-forming polymer.

13. The composition of claim 11, wherein the aqueous phase comprises water and, optionally, at least one water-miscible organic solvent.

14. The composition of claim 13, wherein water is present in the composition in an amount ranging from 5% to 90% by weight, relative to the total weight of the composition.

15. The composition of claim 13, wherein the at least one water-miscible organic solvent is chosen from lower monoalcohols comprising from 1 to 5 carbon atoms, glycols comprising from 2 to 8 carbon atoms, $C_3$-$C_4$ ketones, and $C_2$-$C_4$ aldehydes.

16. The composition of claim 13, wherein the at last one water-miscible organic solvent is chosen from ethanol, isopropanol, propylene glycol, ethylene glycol, 1,3-butylene glycol, and dipropylene glycol.

17. The composition of claim 1, wherein the at least one second polymer is present in the form of particles dispersed in an aqueous phase.

18. The composition of claim 1, further comprising a liquid fatty phase.

19. The composition of claim 18, wherein the liquid fatty phase comprises at least one oil chosen from mineral oils, animal oils, plant oils, synthetic oils, hydrocarbon-based oils, fluorinated and/or silicone-based oils, and mixtures thereof.

20. The composition of claim 18, wherein the liquid fatty phase comprises at least one oil that is volatile at room temperature.

21. The composition of claim 18, wherein the liquid fatty phase comprises a volatile oil chosen from hydrocarbon-based volatile oils comprising from 8 to 16 carbon atoms.

22. The composition of claim 20, wherein the volatile oil is present in the composition in an amount ranging from 0.1% to 98% by weight, relative to the total weight of the composition.

23. The composition of claim 22, wherein the volatile oil is present in the composition in an amount ranging from 1% to 65% by weight, relative to the total weight of the composition.

24. The composition of claim 18, wherein the liquid fatty phase is present in the composition in an amount ranging from 2% to 98% by weight, relative to the total weight of the composition.

25. The composition of claim 24, wherein the liquid fatty phase is present in the composition in an amount ranging from 5% to 85% by weight, relative to the total weight of the composition.

26. The composition of claim 1, wherein the at least one second polymer is present in the form of surface-stabilized particles dispersed in a liquid fatty phase.

27. The composition of claim 26, wherein the particles of the at least one second polymer are surface-stabilized with at least one stabilizer chosen from block polymers, grafted-block polymers, grafted polymers, random polymers, and blends thereof.

28. The composition of claim 27, wherein the stabilizer is chosen from grafted-block and block polymers, comprising at least one block resulting from the polymerization of ethylenic monomers comprising at least one optionally conjugated ethylenic bond, and at least one block of a styrene polymer.

29. The composition of claim 1, wherein the at least one second polymer is present in the composition in an amount ranging from 0.1% to 60% by weight, relative to the total weight of the composition.

30. The composition of claim 29, wherein the at least one second polymer is present in the composition in an amount ranging from 10% to 45% by weight, relative to the total weight of the composition.

31. The composition of claim 1, wherein the size of the particles of the at least one second polymer ranges from 5 nm to 600 nm.

32. The composition of claim 31, wherein the size of the particles of the at least one second polymer ranges from 20 nm to 300 nm.

33. The composition of claim 1, further comprising at least one wax.

34. The composition of claim 33, wherein the at least one wax has a melting point ranging from 30° C. to 120° C.

35. The composition of claim 33, wherein the at least one wax is chosen from beeswax, lanolin wax, Chinese insect waxes, rice wax, carnauba wax, candelilla wax, ouricury wax, cork fiber wax, sugar cane wax, Japan wax, sumach wax, montan wax, microcrystalline waxes, paraffin waxes, ozokerites, ceresin wax, lignite wax, polyethylene waxes, waxes obtained by Fisher-Tropsch synthesis, fatty acid esters of glycerides that are solid at 40° C., waxes obtained by catalytic hydrogenation of animal or plant oils containing linear or branched $C_8$-$C_{32}$ fatty chains, silicone waxes, fluoro waxes, and mixtures thereof.

36. The composition of claim 33, wherein the at least one wax is present in the composition in an amount ranging from 0.1% to 50% by weight, relative to the total weight of the composition.

37. The composition of claim 36, wherein the at least one wax is present in the composition in an amount ranging from 0.5% to 30% by weight, relative to the total weight of the composition.

38. The composition of claim 37, wherein the at least one wax is present in the composition in an amount ranging from 1% to 20% by weight, relative to the total weight of the composition.

39. The composition of claim 1, further comprising at least one dyestuff.

40. The composition of claim 39, wherein the at least one dyestuff is chosen from pigments, nacres, liposoluble dyes, water-soluble dyes, and mixtures thereof.

41. The composition of claim 39, wherein the at least one dyestuff is present in the composition in an amount ranging from 0.01% to 50% by weight, relative to the total weight of the composition.

42. The composition of claim 41, wherein the at least one dyestuff is present in the composition in an amount ranging from 0.01% to 30% by weight, relative to the total weight of the composition.

43. The composition of claim 1, further comprising at least one additive chosen from antioxidants, fillers, preserving agents, fragrances, neutralizing agents, thickeners, cosmetic active agents, dermatological active agents, and mixtures thereof.

44. The composition of claim 1, wherein the composition is in a form chosen from mascaras, eyeliners, products for the eyebrows, products for the lips, face powders, eyeshadows, foundations, make-up products for the body, concealer products, nail varnishes, skincare products, and haircare products.

* * * * *